(12) United States Patent  (10) Patent No.: US 8,563,530 B2
Chang et al.  (45) Date of Patent: Oct. 22, 2013

(54) PURINE NUCLEOSIDE PHOSPHORAMIDATE

(75) Inventors: Wonsuk Chang, Princeton, NJ (US);
Devan Naduthambi, Plainsboro, NJ (US); Dhanapalan Nagarathnam, Bethany, CT (US); Ganapati Reddy Pamulapati, Plainsboro, NJ (US); Bruce S. Ross, Plainsboro, NJ (US); Michael Joseph Sofia, Doylestown, PA (US); Hai-Ren Zhang, Ellicott City, MD (US)

(73) Assignee: Gilead Pharmassel LLC, Foster City, CA (US)

( * ) Notice: Subject to any disclaimer, the term of this patent is extended or adjusted under 35 U.S.C. 154(b) by 116 days.

(21) Appl. No.: 13/076,718

(22) Filed: Mar. 31, 2011

(65) Prior Publication Data

US 2011/0257121 A1   Oct. 20, 2011

Related U.S. Application Data

(60) Provisional application No. 61/319,513, filed on Mar. 31, 2010, provisional application No. 61/319,548, filed on Mar. 31, 2010, provisional application No. 61/355,940, filed on Jun. 17, 2010.

(51) Int. Cl.
*A01N 43/04* (2006.01)
*A61K 31/70* (2006.01)
*C07H 19/04* (2006.01)
*C07H 19/20* (2006.01)

(52) U.S. Cl.
USPC .............................. 514/47; 514/48; 536/26.7

(58) Field of Classification Search
None
See application file for complete search history.

(56) References Cited

U.S. PATENT DOCUMENTS

| | | |
|---|---|---|
| 3,798,209 A | 3/1974 | Witkowski |
| 3,852,267 A | 12/1974 | Meyer |
| 3,994,974 A | 11/1976 | Murakami |
| RE29,835 E | 11/1978 | Witkowski |
| 4,797,285 A | 1/1989 | Barenholz |
| 4,814,477 A | 3/1989 | Wijnberg |
| 4,957,924 A | 9/1990 | Beauchamp |
| 5,013,556 A | 5/1991 | Woodle |
| 5,026,687 A | 6/1991 | Yarchoan |
| 5,077,056 A | 12/1991 | Bally |
| 5,077,057 A | 12/1991 | Szoka |
| 5,091,188 A | 2/1992 | Haynes |
| 5,118,820 A | 6/1992 | Hertel |
| 5,145,684 A | 9/1992 | Liversidge |
| 5,149,794 A | 9/1992 | Yatvin |
| 5,154,930 A | 10/1992 | Popescu |
| 5,157,027 A | 10/1992 | Biller |
| 5,192,549 A | 3/1993 | Barenolz |
| 5,194,654 A | 3/1993 | Hostetler |
| 5,213,804 A | 5/1993 | Martin |
| 5,223,263 A | 6/1993 | Hostetler |
| 5,225,212 A | 7/1993 | Martin |
| 5,256,641 A | 10/1993 | Yatvin |
| 5,256,798 A | 10/1993 | Chou |
| 5,277,914 A | 1/1994 | Szoka |
| 5,316,771 A | 5/1994 | Barenholz |
| 5,372,808 A | 12/1994 | Blatt |
| 5,376,380 A | 12/1994 | Kikuchi |
| 5,405,598 A | 4/1995 | Schinazi |
| 5,411,947 A | 5/1995 | Hostetler |
| 5,420,266 A | 5/1995 | Britton |
| 5,426,183 A | 6/1995 | Kjell |
| 5,453,499 A | 9/1995 | Chou |
| 5,462,724 A | 10/1995 | Schinazi |
| 5,463,092 A | 10/1995 | Hostetler |
| 5,496,546 A | 3/1996 | Wang |
| 5,538,865 A | 7/1996 | Reyes |
| 5,543,389 A | 8/1996 | Yatvin |
| 5,543,390 A | 8/1996 | Yatvin |
| 5,543,391 A | 8/1996 | Yatvin |
| 5,549,910 A | 8/1996 | Szoka |
| 5,554,728 A | 9/1996 | Basava |
| 5,567,434 A | 10/1996 | Szoka |
| 5,610,054 A | 3/1997 | Draper |
| 5,633,358 A | 5/1997 | Gruetzke |

(Continued)

FOREIGN PATENT DOCUMENTS

| | | |
|---|---|---|
| CN | 1079473 | 12/1993 |
| CN | 101108870 | 1/2008 |

(Continued)

OTHER PUBLICATIONS

U.S. Appl No. 12/142,536—Pending Claims as of Mar. 31, 2010.
Selected Prosecution Documents from U.S. Appl . No. 12/142,536:
(1) Jun. 19, 2008 Amendment; (2) Oct. 2, 2009 Office Action; (3) Mar. 31, 2010 Amendment; (4) Jul. 8, 2010 Office Action; (5) Dec. 6, 2010 Response; and (6) Dec. 6, 2010 Declaration.
U.S. Appl. No. 12/645,765—Originally filed claims.
U.S. Appl. No. 12/645,821—Originally filed claims.
U.S. Appl. No. 12/645,710—Originally filed claims.

(Continued)

*Primary Examiner* — Traviss C McIntosh, III
(74) *Attorney, Agent, or Firm* — Sheppard, Mullin, Richter & Hampton LLP; Lorna L. Tanner

(57) ABSTRACT

Disclosed herein is a compound represented by formula 1 or its hydrate thereof in crystalline or crystal-like form.

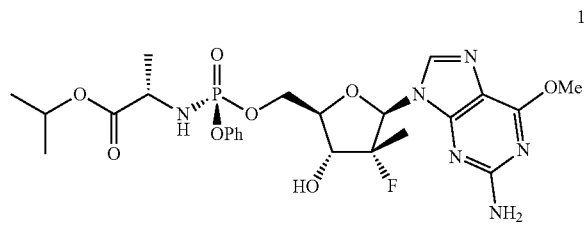

28 Claims, 2 Drawing Sheets

(56) References Cited

U.S. PATENT DOCUMENTS

| | | |
|---|---|---|
| 5,633,388 A | 5/1997 | Diana |
| 5,676,942 A | 10/1997 | Testa |
| 5,695,784 A | 12/1997 | Pollinger |
| 5,703,058 A | 12/1997 | Schinazi |
| 5,711,944 A | 1/1998 | Gilbert |
| 5,725,859 A | 3/1998 | Omer |
| 5,736,155 A | 4/1998 | Bally |
| 5,738,845 A | 4/1998 | Imakawa |
| 5,738,846 A | 4/1998 | Greenwald |
| 5,747,646 A | 5/1998 | Hakimi |
| 5,767,097 A | 6/1998 | Tam |
| 5,792,834 A | 8/1998 | Hakimi |
| 5,827,533 A | 10/1998 | Needham |
| 5,830,455 A | 11/1998 | Valtuena |
| 5,830,905 A | 11/1998 | Diana |
| 5,834,594 A | 11/1998 | Hakimi |
| 5,837,257 A | 11/1998 | Tsai |
| 5,846,964 A | 12/1998 | Ozeki |
| 5,849,696 A | 12/1998 | Chretien |
| 5,869,253 A | 2/1999 | Draper |
| 5,882,679 A | 3/1999 | Needham |
| 5,891,468 A | 4/1999 | Martin |
| 5,891,874 A | 4/1999 | Colacino |
| 5,905,070 A | 5/1999 | Schinazi |
| 5,908,621 A | 6/1999 | Glue |
| 5,922,757 A | 7/1999 | Chojkier |
| 5,928,636 A | 7/1999 | Alber |
| 5,942,223 A | 8/1999 | Bazer |
| 5,980,884 A | 11/1999 | Blatt |
| 5,990,276 A | 11/1999 | Zhang |
| 6,004,933 A | 12/1999 | Spruce |
| 6,034,134 A | 3/2000 | Gold |
| 6,043,077 A | 3/2000 | Barber |
| 6,056,961 A | 5/2000 | Lavie |
| 6,060,080 A | 5/2000 | Kikuchi |
| 6,090,932 A | 7/2000 | McGee |
| 6,130,326 A | 10/2000 | Ramasamy |
| 6,132,763 A | 10/2000 | Fisher |
| 6,143,321 A | 11/2000 | Needham |
| 6,156,501 A | 12/2000 | McGall |
| 6,180,134 B1 | 1/2001 | Zalipsky |
| 6,200,598 B1 | 3/2001 | Needham |
| 6,214,375 B1 | 4/2001 | Modi |
| 6,224,903 B1 | 5/2001 | Martin |
| 6,232,300 B1 | 5/2001 | Schinazi |
| 6,239,159 B1 | 5/2001 | Brown |
| 6,267,985 B1 | 7/2001 | Chen |
| 6,294,192 B1 | 9/2001 | Patel |
| 6,296,870 B1 | 10/2001 | Needham |
| 6,348,587 B1 | 2/2002 | Schinazi |
| 6,372,883 B1 | 4/2002 | Attwood |
| 6,383,471 B1 | 5/2002 | Chen |
| 6,391,859 B1 | 5/2002 | Schinazi |
| 6,395,300 B1 | 5/2002 | Straub |
| 6,410,531 B1 | 6/2002 | Llinas-Brunet |
| 6,420,380 B2 | 7/2002 | Llinas-Brunet |
| 6,455,513 B1 | 9/2002 | McGuigan |
| 6,455,690 B1 | 9/2002 | Tam |
| 6,475,985 B1 | 11/2002 | Wagner |
| 6,479,463 B1 | 11/2002 | Wang |
| 6,495,677 B1 | 12/2002 | Ramasamy |
| 6,509,320 B1 | 1/2003 | Wang |
| 6,534,523 B1 | 3/2003 | Bailey |
| 6,552,183 B1 | 4/2003 | Ramasamy |
| 6,555,677 B2 | 4/2003 | Petrillo |
| 6,569,463 B2 | 5/2003 | Patel |
| 6,573,248 B2 | 6/2003 | Ramasamy |
| 6,635,278 B1 | 10/2003 | Dahl |
| 6,642,206 B2 | 11/2003 | Ramasamy |
| 6,645,528 B1 | 11/2003 | Straub |
| 6,653,455 B1 | 11/2003 | Johdo |
| 6,660,721 B2 | 12/2003 | Devos |
| 6,677,314 B2 | 1/2004 | Klecker |
| 6,677,315 B2 | 1/2004 | Klecker |
| 6,680,068 B2 | 1/2004 | Jain |
| 6,680,303 B2 | 1/2004 | Schinazi |
| 6,682,715 B2 | 1/2004 | Klecker |
| 6,683,045 B2 | 1/2004 | Klecker |
| 6,703,374 B1 | 3/2004 | Katki |
| 6,726,925 B1 | 4/2004 | Needham |
| 6,753,309 B2 | 6/2004 | Klecker |
| 6,777,395 B2 | 8/2004 | Bhat |
| 6,784,166 B2 | 8/2004 | Devos |
| 6,787,305 B1 | 9/2004 | Li |
| 6,787,526 B1 | 9/2004 | Bryant |
| 6,812,219 B2 | 11/2004 | LaColla |
| 6,815,542 B2 | 11/2004 | Hong |
| 6,846,810 B2 | 1/2005 | Martin |
| 6,897,201 B2 | 5/2005 | Boyer |
| 6,908,924 B2 | 6/2005 | Watanabe |
| 6,911,424 B2 | 6/2005 | Schinazi |
| 6,914,054 B2 | 7/2005 | Sommadossi |
| 6,923,988 B2 | 8/2005 | Patel |
| 6,932,983 B1 | 8/2005 | Straub |
| 6,962,991 B2 | 11/2005 | Dempcy |
| 6,977,257 B2 | 12/2005 | Parab |
| 7,018,985 B1 | 3/2006 | Boyer |
| 7,018,989 B2 | 3/2006 | McGuigan |
| 7,060,294 B2 | 6/2006 | Batra |
| 7,060,689 B2 | 6/2006 | Goins |
| 7,070,801 B2 | 7/2006 | Yamazaki |
| 7,081,449 B2 | 7/2006 | Pietrzkowski |
| 7,105,493 B2 | 9/2006 | Sommadossi |
| 7,105,499 B2 | 9/2006 | Carroll |
| 7,125,855 B2 | 10/2006 | Bhat |
| 7,148,206 B2 | 12/2006 | Sommadossi |
| 7,163,929 B2 | 1/2007 | Sommadossi |
| 7,202,224 B2 | 4/2007 | Eldrup |
| 7,217,523 B2 | 5/2007 | Wagner |
| 7,268,119 B2 | 9/2007 | Cook |
| 7,307,065 B2 | 12/2007 | Schinazi |
| 7,323,453 B2 | 1/2008 | Olsen |
| 7,365,057 B2 | 4/2008 | LaColla |
| 7,390,791 B2 | 6/2008 | Becker |
| 7,429,572 B2 | 9/2008 | Clark |
| 7,462,608 B2 | 12/2008 | Chen |
| 7,601,820 B2 | 10/2009 | Wang |
| 7,608,597 B2 | 10/2009 | Sommadossi |
| 7,608,600 B2 | 10/2009 | Storer |
| 7,635,689 B2 | 12/2009 | LaColla |
| 7,754,699 B2 | 7/2010 | Chun |
| 7,879,815 B2 | 2/2011 | MacCoss |
| 7,964,580 B2 | 6/2011 | Sofia |
| 8,173,621 B2 | 5/2012 | Du |
| 8,334,270 B2 | 12/2012 | Sofia |
| 2001/0034440 A1 | 10/2001 | Shepard |
| 2002/0058635 A1 | 5/2002 | Averett |
| 2002/0142050 A1 | 10/2002 | Straub |
| 2002/0198173 A1 | 12/2002 | Schinazi |
| 2003/0050229 A1 | 3/2003 | Sommadossi |
| 2003/0060400 A1 | 3/2003 | LaColla |
| 2003/0120071 A1 | 6/2003 | McGuigan |
| 2003/0144502 A1 | 7/2003 | Pietrzkowski |
| 2003/0153744 A1 | 8/2003 | Mekouar |
| 2003/0187018 A1 | 10/2003 | Llinas-Brunet |
| 2004/0006007 A1 | 1/2004 | Gosselin |
| 2004/0014108 A1 | 1/2004 | Eldrup |
| 2004/0023240 A1 | 2/2004 | Marliere |
| 2004/0023901 A1 | 2/2004 | Cook |
| 2004/0038993 A1 | 2/2004 | Shipps |
| 2004/0059104 A1 | 3/2004 | Cook |
| 2004/0063622 A1 | 4/2004 | Sommadossi |
| 2004/0067901 A1 | 4/2004 | Bhat |
| 2004/0072788 A1 | 4/2004 | Bhat |
| 2004/0097461 A1 | 5/2004 | Sommadossi |
| 2004/0097462 A1 | 5/2004 | Sommadossi |
| 2004/0101535 A1 | 5/2004 | Sommadossi |
| 2004/0102414 A1 | 5/2004 | Sommadossi |
| 2004/0110717 A1 | 6/2004 | Carroll |
| 2004/0142980 A1 | 7/2004 | Finzel |
| 2004/0167140 A1 | 8/2004 | Schinazi |
| 2004/0191824 A1 | 9/2004 | Dempcy |
| 2004/0214844 A1 | 10/2004 | Otto |
| 2004/0224917 A1 | 11/2004 | Dahl |

(56) References Cited

U.S. PATENT DOCUMENTS

| | | |
|---|---|---|
| 2004/0229839 A1 | 11/2004 | Babu |
| 2004/0229840 A1 | 11/2004 | Bhat |
| 2004/0248892 A1 | 12/2004 | Wang |
| 2004/0254141 A1 | 12/2004 | Schinazi |
| 2004/0259934 A1 | 12/2004 | Olsen |
| 2004/0265969 A1 | 12/2004 | Li |
| 2004/0266996 A1 | 12/2004 | Rabi |
| 2005/0009737 A1 | 1/2005 | Clark |
| 2005/0020825 A1 | 1/2005 | Storer |
| 2005/0026853 A1 | 2/2005 | Mekouar |
| 2005/0031588 A1 | 2/2005 | Sommadossi |
| 2005/0048116 A1 | 3/2005 | Straub |
| 2005/0058710 A1 | 3/2005 | Straub |
| 2005/0075309 A1 | 4/2005 | Storer |
| 2005/0080034 A1 | 4/2005 | Standring |
| 2005/0090432 A1 | 4/2005 | McPhee |
| 2005/0090660 A1 | 4/2005 | Watanabe |
| 2005/0119189 A1 | 6/2005 | Cottrell |
| 2005/0124532 A1 | 6/2005 | Sommadossi |
| 2005/0130931 A1 | 6/2005 | Boyer |
| 2005/0137161 A1 | 6/2005 | Sommadossi |
| 2005/0148534 A1 | 7/2005 | Castellino |
| 2005/0154056 A1 | 7/2005 | Yang |
| 2005/0164960 A1 | 7/2005 | Olsen |
| 2005/0215513 A1 | 9/2005 | Boojamra |
| 2005/0215614 A1 | 9/2005 | Singh |
| 2005/0227947 A1 | 10/2005 | Chen |
| 2005/0228013 A1 | 10/2005 | Thurkauf |
| 2005/0261237 A1 | 11/2005 | Boojamra |
| 2005/0267018 A1 | 12/2005 | Blatt |
| 2006/0003951 A1 | 1/2006 | Mekouar |
| 2006/0014943 A1 | 1/2006 | Dempcy |
| 2006/0034937 A1 | 2/2006 | Patel |
| 2006/0035866 A1 | 2/2006 | Cannizzaro |
| 2006/0040890 A1 | 2/2006 | Martin |
| 2006/0040927 A1 | 2/2006 | Blake |
| 2006/0040944 A1 | 2/2006 | Gosselin |
| 2006/0057196 A1 | 3/2006 | Hussain |
| 2006/0079478 A1 | 4/2006 | Boojamra |
| 2006/0100166 A1 | 5/2006 | De Koning |
| 2006/0110727 A9 | 5/2006 | McGall |
| 2006/0122146 A1 | 6/2006 | Chun |
| 2006/0122154 A1 | 6/2006 | Olsen |
| 2006/0142238 A1 | 6/2006 | McGuigan |
| 2006/0166964 A1 | 7/2006 | Hudyma |
| 2006/0188570 A1 | 8/2006 | Batra |
| 2006/0194749 A1 | 8/2006 | Keicher |
| 2006/0199783 A1 | 9/2006 | Wang |
| 2006/0234962 A1 | 10/2006 | Olsen |
| 2006/0241064 A1 | 10/2006 | Roberts |
| 2006/0241071 A1 | 10/2006 | Grinstaff |
| 2006/0252715 A1 | 11/2006 | Keicher |
| 2006/0264389 A1 | 11/2006 | Bhat |
| 2006/0264404 A1 | 11/2006 | Boojamra |
| 2006/0276511 A1 | 12/2006 | Serrano-Wu |
| 2006/0287300 A1 | 12/2006 | Klein |
| 2006/0293306 A1 | 12/2006 | Beaulieu |
| 2007/0015905 A1 | 1/2007 | LaColla |
| 2007/0026073 A1 | 2/2007 | Doney |
| 2007/0037735 A1 | 2/2007 | Gosselin |
| 2007/0037773 A1 | 2/2007 | Sommadossi |
| 2007/0042939 A1 | 2/2007 | LaColla |
| 2007/0042988 A1 | 2/2007 | Klumpp |
| 2007/0042990 A1 | 2/2007 | Gosselin |
| 2007/0049754 A1 | 3/2007 | Boojamra |
| 2007/0054842 A1 | 3/2007 | Blatt |
| 2007/0059360 A1 | 3/2007 | Jaiswal |
| 2007/0060498 A1 | 3/2007 | Gosselin |
| 2007/0060541 A1 | 3/2007 | Gosselin |
| 2007/0077295 A1 | 4/2007 | Dahl |
| 2007/0087960 A1 | 4/2007 | Storer |
| 2007/0099902 A1 | 5/2007 | Dahl |
| 2007/0155731 A1 | 7/2007 | Butora |
| 2007/0197463 A1 | 8/2007 | Chun |
| 2007/0225249 A1 | 9/2007 | Shi |
| 2007/0265222 A1 | 11/2007 | MacCoss |
| 2007/0265262 A1 | 11/2007 | Schmitz |
| 2007/0275912 A1 | 11/2007 | Bhat |
| 2007/0275947 A1 | 11/2007 | Bergstrom |
| 2008/0014228 A1 | 1/2008 | Darmuzey |
| 2008/0021047 A1 | 1/2008 | Butora |
| 2008/0139802 A1 | 6/2008 | Axt |
| 2008/0182863 A1 | 7/2008 | Simmen |
| 2008/0200423 A1 | 8/2008 | Cook |
| 2008/0280850 A1 | 11/2008 | Sommadossi |
| 2009/0004138 A1 | 1/2009 | Francom |
| 2009/0105302 A1 | 4/2009 | Simmen |
| 2009/0131460 A1 | 5/2009 | Simmen |
| 2009/0137521 A1 | 5/2009 | Hamilton |
| 2009/0156595 A1 | 6/2009 | Raboisson |
| 2009/0176732 A1 | 7/2009 | Beigelman |
| 2009/0233879 A1 | 9/2009 | Reddy |
| 2009/0280084 A1 | 11/2009 | Schinazi |
| 2009/0281140 A1 | 11/2009 | Simmen |
| 2009/0281141 A1 | 11/2009 | Simmen |
| 2009/0306007 A1 | 12/2009 | Wagner |
| 2010/0022468 A1 | 1/2010 | Meppen |
| 2010/0029008 A1 | 2/2010 | Rojas Stutz |
| 2010/0035835 A1 | 2/2010 | Narjes |
| 2010/0081628 A1 | 4/2010 | Du |
| 2010/0120855 A1 | 5/2010 | Simmen |
| 2010/0137576 A1 | 6/2010 | Stec |
| 2010/0152128 A1 | 6/2010 | Attenni |
| 2010/0173863 A1 | 7/2010 | Schinazi |
| 2010/0227801 A1 | 9/2010 | Hopkins |
| 2010/0279973 A1 | 11/2010 | Chun |
| 2010/0286083 A1* | 11/2010 | Bao et al. ......................... 514/47 |
| 2010/0298257 A1 | 11/2010 | Ross |
| 2010/0316594 A1 | 12/2010 | Sommadossi |
| 2011/0015146 A1* | 1/2011 | Sofia et al. ....................... 514/48 |
| 2011/0124592 A1 | 5/2011 | McGuigan |
| 2011/0130440 A1 | 6/2011 | Manoharan |
| 2011/0229438 A1 | 9/2011 | Dragovich |
| 2011/0257121 A1 | 10/2011 | Chang |
| 2011/0257122 A1 | 10/2011 | Sofia |
| 2012/0142626 A1 | 6/2012 | Du |
| 2012/0258928 A1 | 10/2012 | Du |
| 2012/0316327 A1 | 12/2012 | Chun |
| 2013/0029929 A1 | 1/2013 | Sofia |

FOREIGN PATENT DOCUMENTS

| | | |
|---|---|---|
| EP | 0 180 276 | 7/1986 |
| EP | 0 350 287 | 1/1990 |
| EP | 0 524 579 | 1/1993 |
| EP | 1 881 001 | 1/2008 |
| EP | 2207786 | 3/2012 |
| JP | 05-238939 | 9/1993 |
| WO | WO-89/02733 | 4/1989 |
| WO | WO-90/00555 | 1/1990 |
| WO | WO-91/16920 | 11/1991 |
| WO | WO-91/18914 | 12/1991 |
| WO | WO-91/19721 | 12/1991 |
| WO | WO-93/00910 | 1/1993 |
| WO | WO-94/26273 | 11/1994 |
| WO | WO-95/13090 | 5/1995 |
| WO | WO-95/24185 | 9/1995 |
| WO | WO-96/15132 | 5/1996 |
| WO | WO 96/32403 | 10/1996 |
| WO | WO-97/12033 | 4/1997 |
| WO | WO-97/36554 | 10/1997 |
| WO | WO-98/16184 | 4/1998 |
| WO | WO-98/17679 | 4/1998 |
| WO | WO-98/22496 | 5/1998 |
| WO | WO-99/07734 | 2/1999 |
| WO | WO-99/15194 | 4/1999 |
| WO | WO-99/32139 | 7/1999 |
| WO | WO-99/32140 | 7/1999 |
| WO | WO-99/43691 | 9/1999 |
| WO | WO-99/59621 | 11/1999 |
| WO | WO-99/64016 | 12/1999 |
| WO | WO-00/06529 | 2/2000 |
| WO | WO-00/09531 | 2/2000 |
| WO | WO-00/37110 | 6/2000 |

(56) References Cited

FOREIGN PATENT DOCUMENTS

| | | |
|---|---|---|
| WO | WO-01/32153 | 5/2001 |
| WO | WO-02/48172 | 6/2001 |
| WO | WO-01/60315 | 8/2001 |
| WO | WO-01/79246 | 10/2001 |
| WO | WO-01/81359 | 11/2001 |
| WO | WO-01/90121 | 11/2001 |
| WO | WO-01/91737 | 12/2001 |
| WO | WO-01/92282 | 12/2001 |
| WO | WO-01/96353 | 12/2001 |
| WO | WO-02/08187 | 1/2002 |
| WO | WO-02/08198 | 1/2002 |
| WO | WO-02/08251 | 1/2002 |
| WO | WO-02/08256 | 1/2002 |
| WO | WO-02/18404 | 3/2002 |
| WO | WO-02/32414 | 4/2002 |
| WO | WO-02/32920 | 4/2002 |
| WO | WO-02/48116 | 6/2002 |
| WO | WO-02/48157 | 6/2002 |
| WO | WO-02/48165 | 6/2002 |
| WO | WO-02/057287 | 7/2002 |
| WO | WO-02/057425 | 7/2002 |
| WO | WO-02/060926 | 8/2002 |
| WO | WO-02/100415 | 12/2002 |
| WO | WO-03/000713 | 1/2003 |
| WO | WO-03/006490 | 1/2003 |
| WO | WO-03/010141 | 2/2003 |
| WO | WO-03/011877 | 2/2003 |
| WO | WO-03/024461 | 3/2003 |
| WO | WO-03/026589 | 4/2003 |
| WO | WO-03/037895 | 5/2003 |
| WO | WO-03/051899 | 6/2003 |
| WO | WO-03/053989 | 7/2003 |
| WO | WO-03/061576 | 7/2003 |
| WO | WO-03/062256 | 7/2003 |
| WO | WO-03/064456 | 8/2003 |
| WO | WO-03/068244 | 8/2003 |
| WO | WO-03/105770 | 12/2003 |
| WO | WO-03/106477 | 12/2003 |
| WO | WO-2004/000858 | 12/2003 |
| WO | WO-2004/002422 | 1/2004 |
| WO | WO-2004/002940 | 1/2004 |
| WO | WO-2004/002944 | 1/2004 |
| WO | WO-2004/002999 | 1/2004 |
| WO | WO-2004/003000 | 1/2004 |
| WO | WO-2004/009610 | 1/2004 |
| WO | WO-2004/011478 | 2/2004 |
| WO | WO-2004/014313 | 2/2004 |
| WO | WO-2004/014852 | 2/2004 |
| WO | WO-2004/041201 | 5/2004 |
| WO | WO-2004/065367 | 8/2004 |
| WO | WO-2004/080466 | 9/2004 |
| WO | WO-2004/096210 | 11/2004 |
| WO | WO-2004/096234 | 11/2004 |
| WO | WO-2004/096235 | 11/2004 |
| WO | WO-2004/096286 | 11/2004 |
| WO | WO-2004/106356 | 12/2004 |
| WO | WO-2005/009418 | 2/2005 |
| WO | WO-2005/020884 | 3/2005 |
| WO | WO-2005/037214 | 4/2005 |
| WO | WO-2005/082144 | 9/2005 |
| WO | WO-2005/087788 | 9/2005 |
| WO | WO-2005/095403 | 10/2005 |
| WO | WO-2005/103045 | 11/2005 |
| WO | WO-2006/000922 | 1/2006 |
| WO | WO-2006/012440 | 2/2006 |
| WO | WO-2006/020082 | 2/2006 |
| WO | WO-2006/029081 | 3/2006 |
| WO | WO-2006/035061 | 4/2006 |
| WO | WO-2006/065335 | 6/2006 |
| WO | WO-2006/065590 | 6/2006 |
| WO | WO 2006/119347 | 11/2006 |
| WO | WO 2006121820 | 11/2006 |
| WO | WO-2007/002602 | 1/2007 |
| WO | WO-2007/014925 | 2/2007 |
| WO | WO-2007/020193 | 2/2007 |
| WO | WO-2007/027248 | 3/2007 |
| WO | WO-2007/039142 | 4/2007 |
| WO | WO-2007/039145 | 4/2007 |
| WO | WO-2007/065829 | 6/2007 |
| WO | WO-2007/076034 | 7/2007 |
| WO | WO-2007/088148 | 8/2007 |
| WO | WO-2007/092000 | 8/2007 |
| WO | WO-2007/093901 | 8/2007 |
| WO | WO-2008/010921 | 1/2008 |
| WO | WO-2008/045419 | 4/2008 |
| WO | WO-2008/062206 | 5/2008 |
| WO | WO-2008/082601 | 7/2008 |
| WO | WO 2008121634 | 10/2008 |
| WO | WO-2009/115893 | 9/2009 |
| WO | WO-2009/129120 | 10/2009 |
| WO | WO 2010/075549 | 7/2010 |
| WO | WO-2010/075554 | 7/2010 |
| WO | WO-2010/080878 | 7/2010 |
| WO | WO 2010075517 | 7/2010 |
| WO | WO 2010075549 | 7/2010 |
| WO | WO 2010/130726 | 11/2010 |
| WO | WO 2011/123668 | 10/2011 |

OTHER PUBLICATIONS

International Search Report of PCT/US2011/030767 mailed Aug. 10, 2011.
Written Opinion of PCT/US2011/030767 mailed Aug. 10, 2011.
Aquaro et al., Antimicrobial Agents and Chemotherapy (2000) 1: 173-177.
Byrn et al,. Pharmaceutical Research (1995) 12(7) 945-954.
Chapman et al., Nucleotides, Nucleosides and Nucleic Acids (2001) 20(4-7): 621-628.
Chapman et al., Nucleotides, Nucleosides and Nucleic Acids (2001) 20(4-7): 1085-1090.
Chawla et al., CRIPS (2004) 5(1): 9-12.
Clark et al., J. Med. Chem. (2005) 48(17): 5504-5508.
Eisenberg et al., Nucleosides, Nucleotides & Nucleic Acids (2001) 20(4-7): 1091-1098.
Haleblian, J. Pharm. Sci. (1975) 64(8): 1269-1288.
Howes et al., Nucleosides, Nucleotides and Nucleic Acids (2003) 22(5): 687-689.
J.K. Guillory Polymorphism in Pharmaceutical Solids (1999); pp. 183-226; H.G. Brittain (Ed.); Marcel Dekker, Inc. (New York).
Lee et al., Antimicrobial Agents and Chemotherapy (2005) 49(5): 1898-1906.
Ma et al., J. Biol. Chem. (2007) 282(41): 29812-29820.
McGuigan et al., Antiviral Chemistry and Chemotherapy (1998) 9: 473-479.
McGuigan et al., Biorg. Med. Chem. (2005) 13: 3219-3227.
Murakami et al., Antiviral Chemistry & Chemotherapy (2007) 51(2): 503-509.
Murakami et al., Antimicrobial Agents and Chemotherapy (2008) 52(2): 458-464.
Perrone et al., J. Med. Chem. (2007) 50(8): 1840-1849.
Ray et al., Antimicrobial Agents and Chemotherapy (2008) 52(2): 648-654.
Stuyver et al., Antiviral Chemistry & Chemotherapy (2004) 48(2): 651-654.
Abraham, et al., "Synthesis and Biological Activity of Aromatic Amino Acid Phosphoramidates of 5-Fluoro-2'- deoxyuridine and 1-Beta-Arabinofuranosylcytosine: Evidence of Phosphoramidase Activity," J. Med. Chem., (1996), 39:4569-4575.
Abraham, et al., "Synthesis, Biological Activity and Decomposition Studies of Amino Acid Phosphomonoester Amidates of Acyclovir" Nucleosides, Nucleotides and Nucleic Acids, (1997), 16(10):2079-2092.
Asif, et al., "Pharmacokinetics of the Antiviral Agent B-D-2'-Deoxy-2'-Fluoro-2'-C-Methylcytidine in Rhesus Monkeys," Antimicrobial Agents and Chemotherapy, (2007), 51(8):2877-2882.
Balzarini, et al., "Mechanism of anti-HIV action of masked alaninyl d4t-MP derivatives," PNAS, (1996), 93:7295-7299.
Banker, G.S., "Modern Pharmaceutics, 3ed.", Marcel Dekker, New York, (1996), 451 and 596.
Bartenschlager, et al., "Kinetic and Structural Analyses of Hepatitis C Virus Polyprotein Processing," J. Virol., (1994), 68(8):5045-5055.

(56) References Cited

OTHER PUBLICATIONS

Bartenschlager, et al., "Nonstructural Protein 3 of the Hepatitis C Virus Encodes a Serine-Type Proteinase Requried for Cleavage at the N53/4 and NS4/5 Junctions," J. Virol., (1993), 67(7):38353844.

Baschang, et al., Neue Derivate von Thymidin-3',5'-cyclophosphat, Angew. Chem., (1973), 85(1):44-45.

Battaglia, et al., "Combination Therapy with Interferon and Ribavirin in the Treatment of Chronic Hepatitis C Infection," the Annals of Pharmacotherapy, (2000), 34(4):487-494.

Bazan, et al., "Detection of a Trypsin-like Serine Protease Domain in Flaviviruses and Pestiviruses," Virology, (1989), 171:637-639.

Beaulieu, et al., "Inhibitors of the HCV NS5B polymerase: New hope for the treatment of hepatitis C infections," Current Opinion in Investigational Drugs, (2004), 5(8):838-850.

Behrens, et al., "Indentification and properties of the RNA-dependent RNA polymerase of hepatitis C virus," EMBO, (1996), 15(1):12-22.

Berenguer, et al., "Hepatitis C virus in the transplant setting," Antiviral Therapy. Second International Conference on Therapies for Viral Hepatitis, (1998), 3(3):125-136.

Beres, et al., "Synthesis and Antitumor and Antiviral Properties of 5-Alkyl-2'-deoxyuridines, 3',5'-Cyclic Monophosphates, and Neutral Cyclic Triesters," J. Med. Chem., (1986), 29(4):494-499.

Beres, et al., Synthesis and Antitumor and Antiviral Properties of 5-Halo- and 5-(Trifluoromethyl)-2'- deoxyuridine 3',5-Cyclic Monophosphates and Neutral Triesters, J. Med. Chem., (1986), 29: 1243-1249.

Bhat, et al., "Synthesis and Pharmacokinetic Properties of Nucleoside Analogues as Possible Inhibitors of HCV RNA Replication," (Oral Session V: Hepatitis C Virus, Flaviviruses), 16th International Conference on Antiviral Research, Abstract No. 120, p. A75 (April27-May 1, 2003, Savannah, GA.

Broeders, et al., "A 400- and 600-MHz 1H NMR Conformational Study on Nucleoside Cyclic 3',5'Pv-TBP Systems. Conformational Transmission Induces Diequatorial Orientation of the 3',5-Dioxaphosphorinane Ring in a Nonchair Conformation," J. Am. Chem. Soc., (1990), 112:7475-7482.

Broeders, et al., 2'-O-Methyl-cis-adenosine 3',5'-cyclic methyl monophosphate, a new model system for cAMP. Aspects of structure and reactivity, Can J. Chem., (1993), 71:855-863.

Byrn, et al., "Hydrates and Solvates," Solid State Chemistry of Drugs, 2d Chapter 11, (2003), 233-247.

Calisher, et al., "Antigenic Relationships between Flaviviruses as Determined by Cross-neutralization Tests with Polyclonal Antisera," J. Gen. Virol., (1989), 70:37-43.

Carroll, et al., "Nucleoside Analog Inhibitors of Hepatitis C Virus Replication," Infectious Disorders -Drug Targets, (2006), 6:17-29.

Chang, et al., "Amino Acid Phosphoramidate Monoesters of 3'-Azido-3'-deoxythymidine: Relationship between Antiviral Potency and Intracellular Metabolism," J. Med. Chem., (2001), 44:223-231.

Chen, et al., "In Vivo Pharmacokinetics and Metabolism of Anti-Human Immunodeficiency Virus Agent D4t-5'-[P-Bromophenyl Methoxyalaninyl Phosphate] (Sampidine) in Mice," Drug Metabolism and Disposition, (2001), 29(7):1035-1041.

Chen, et al., "Metabolism of Stavudine-5'-[P-Bromophenyl Methoxyalaninyl Phosphate], Stampidine, in Mice, Dogs, and Cats," Drug Metabolism and Disposition, (2002), 30(12):1523-1531.

Chou, et al., "Evidence that Human Histidine Triad Nucleotide Binding Protein 3 (Hint3) is a Distinct Branch of the Histidine Triad (HIT) Super family," J. Mol. Biol., (2007), 373:978-989.

Chou, et al., "Phosphoramidate Pronucleotides: A Comparison of the Phosphoramidase Substrate Specificity of Human and *Escherichia coli* Histidine Triad Nucleotide Binding Proteins," Molecular Pharmaceutics, (2007), 4(2):208-217.

Chu, et al., "Isolation and Structure of SCH 351633: A Novel Hepatitis C Virus (HCV) NS3 Protease Inhibitor from the Fungus Penicillium Griseofulvum," Bioorganic & Medicinal Chemistry Letters, (1999), 9:1949-1952.

Chu, et al., "Structure of Sch 68631: A New Hepatitis C virus Proteinase Inhibitor from Streptomyces sp." Tetrahedron Letters, (1996), 37(40): 7229-7232.

Cihlar, et al., "Design and Profiling of Gs-9148, a Novel Nucleotide Analog Active against Nucleoside-Resistant Variants of Human Immunodeficiency Virus Type 1, and Its Orally Bioavailable Phosphonoamidate Prodrug, GS-9131," Antimicrobial Agents and Chemotherapy, (2008), 52(2):655-665.

Congiatu, et al., "Molecular Modelling Studies on the Binding of Some Protides to the Putative Human Phosphoramidase Hint1," Nucleosides, Nucleotides and Nucleic Acids, (2007), 26(8):1121-1124.

Congiatu, et al., "Naphthyl Phosphoramidate Derivatives of BVdU as Potential Anticancer Agents: Design, Synthesis and Biological Evaluation," Nucleosides, Nucleotides, and Nucleic Acids, (2005), 24(5-7):485-489.

Curley, et al., "Synthesis and anti-HIV evaluation of some phosphoramidate derivatives of AZT: studies on the effect of chain elongation on biological activity," Antiviral Research, (1990), 14:345-356.

Davis, G.L., "Current Therapy for Chronic Hepatitis C," Gastroenterology, (2000), 118:S104-S114.

D'Cruz, et al., "Stampidine: a selective oculo-genital microbicide," Journal of Antimicrobial Chemotherapy, (2005), 56:10-19.

De Lombaert, et al., "N-Phosphonomethyl Dipeptides and Their Phosphonate Prodrugs, a New Generation of Neutral Endopeptidase (NEP, EC 3.4.24.11) Inhibitors," J. Med. Chem., (1994), 37(4):498-511.

Drontle, et al., "Designing a Pronucleotide Stratagem: Lessons from Amino Acid Phosphoramidates of Anticancer and Antiviral Pyrimidines," MiniReviews in Medicinal Chemistry, (2004), 4:409-419.

Eckart, et al., "The hepatitis C virus encodes a serine protease involved in processing of the putative nonstructural proteins from the viral polyprotein precursor," Biochem. Biophys. Res. Comm., (1993), 192(2):399-406.

Edmundson, et al., "Cyclic Organophosphorus Compounds. Part 23. Configurational Assignments in the 4-Phenyl-1,3, 2o—dioxaphosphorinane Series. X-Ray Molecular Structure of cis-2-Benzylamino-4- phenyl-1,3,2-dioxaphosphorinane," J. Chem. Res. Synop., (1989), 122-123.

Egron, et al., "S-Acyl-2-thioethyl Phosphoramidate Diester Derivatives as Mononucleotide Prodrugs." J. Med. Chem., (2003), 46:4564-4571.

Eldrup, et al., "Structure Activity Relationship of 2' Modified Nucleosides for Inhibition of Hepatitis C Virus," (Oral Session V: Hepatitis C Virus, Flaviviruses), 16th International Conference on Antiviral Research, Abstract No. 119, p. A75 (Apr. 27-May 1, 2003, Savannah, GA).

Eldrup, et al., "Structure-Activity Relationship of Purine Ribonucleosides for Inhibition of Hepatitis C Virus RNA-Dependent RNA Polymerase," J. Med. Chem., (2004), 47(9):2283-2295.

Engels, et al., "Synthese und Eigenschaften von Uridin-3',5'-cyclophosphat-estern," Chem. Ber., (1977), 110(6):2019-2027 (with English Abstract).

Failla, et al., "Both NS3 and NS4A are required for proteolytic processing of hepatitus C virus nonstructural protein," J. Virol., (1994), 68:3753-3760.

Farquhar, et al., "Synthesis and Biological Evaluation of Neutral Derivatives of 5-Fluoro-2'deoxyuridine 5'-Phosphate," J. Med. Chem., (1983), 26(8):1153-1158.

Farquhar. et al., "Synthesis of Biological Evaluation of 9-[5'-(2-0xo-l,3,2-oxazaphosphorinan-2-yl)- Beta-D-arabinosyl]adenine and 9[5'-(2-0xo-I,3,2-dioxaphosphorinan-2-yl)-Beta-D-arabinosyl]adenine: Potential Neutral Precursors of 9-[Beta-D-Arabinofuranosyl]adenine 5'-Monophosphate," J. Med. Chem., (1985), 28(9):1358-1361.

Fields, et al., "Virology," Editors: Fields, B. N., Knipe, D. M., and Howley, P. M., Lippincott- Raven Publishers, Philadelphia, PA, (1996), Chapter 31:931-959.

(56) References Cited

OTHER PUBLICATIONS

Freed, et al., "Evidence for acyloxymethyl esters of pyrimidine 5'-deoxyribonucleotides as extracellular sources of active 5'-deoxyribonucleotides in cultured cells," Biochemical Pharmacology, (1989), 38(9):3193-3198.
Goekjian, et al., "Synthesis of Fluorinated Macrocyclic Bis(indoyl)maleimides as Potential 19F NMR Probes for Protein Kinase C," J. Org. Chem., (1999), 64(12):4238-4246.
Gorbalenya, et al., "A conserved NTP-motif in putive helicases," Nature, (1988), 333:22.
Gorbalenya, et al., "N-termianl domains of putative helicases of flavi-and pestiviruses may be serine proteases," Nucleic Acid Res., (1989), 17(10):3889-3897.
Grakoui, et al., "A second hepatitis C virus-encoded proteinase," Proc. Natl. Acad. Sci., (1993), 90:10583-10587.
Grakoui, et al., "Characterization of the Hepatitis C Virus-Encoded Serine Proteinase: Determination of Proteinase-Dependent Polyprotein Cleavage Sites," J. Virol., (1993), 67(5):28322843.
Griffith, et al., "HCV Anti-viral Agents," Annual Reports in Medicinal Chemistry, (2004), 39:223-237.
Gromova, et al., "Optical rotatory dispersion and circular dichroism of mono- and oligonucleotide-amino acids (amidates)," Biochim. Biophys. Acta, (1971), 240:1-11.
Gunic, et al., "6-Hydrazinopurine 2'-methyl ribonucleosides and their 5'-monophosphate prodrugs as potent hepatitis C virus inhibitors," Bioorg. & Med. Chem. Letters, (2007), 17(9):2456-2458.
Gunic, et al., Cyclic monophosphate prodrugs of base-modified 2'-C-methyl ribonucleosides as potent inhibitors of hepatitis C virus RNA replication, Biorganic & Medicinal Chemistry Letters, (2007), 17:2452-2455.
Halstead, S.B., "Pathogenesis of Dengue: Challenges to Molecular Biology," Science, (1988), 239:476-481.
Halstead, S.B., "Selective Primary Health Care: Strategies for Control of Disease in the Developing World Xl. Dengue," Rev. Infect. Dis., (1984), 6(2):251-264.
Harris, et al., "Synthesis and antiviral evaluation of phosphoramidate derivatives of (E)-5-(2- bromoviny1)-2'-deoxyuridine," Antiviral Chemistry & Chemotherapy, (2002), 12:293-300.
Hernandez, et al., "Synthesis of Highly Functionalized Chiral Nitriles by Radical Fragmentation of Beta-Hydroxy Azides. Convenient Transformation of Aldononitriles into 1,4- and 1,5-Iminoalditols," J, Org. Chem., (2004), 69(24):8437-8444.
Hertel, et al., "Synthesis of 2-Deoxy-2,2-difluoro-D-ribose and 2-Deoxy-2,2-difluoro-D-ribofuranosyl Nucleosides," J. Org. Chem., (1988), 53:2406-2409.
Hijikata, et al., "Two Distinct Proteinase Activites Required for the Processing of a Putative Nonstructural Precursor Protein of Hepatitis C Virus," J. Virol., (1993), 67(8):4665-4675.
Hooz, et al., "A rapid, mild procedure for the preparation of alkyl chlorides and bromides," Can. J. Chem., (1968), 46:86-87.
Hostetler, et al., "Greatly Enhanced Inhibition of Human Immunodeficiency Virus Type 1 Replication in CEM and HT4-6C by 3'-Deoxythymidine Diphosphate Dimyristoylglycerol, a Lipid Prodrug of 3'-Deoxythymidine," Antimicrob. Agents Chemother., (1992), 36(9):2025-2029.
Hostetler, et al., "Synthesis and Antiretroviral Activity of Phospholipid Analogs of Azidothymidine and Other Antiviral Nucleosides," J. Biol. Chem., (1990), 265(11):6112-6117.
Hunston, et al., "Synthesis and Biological Properties of Some Cyclic Phosphotriesters Derived from 2'-Deoxy-5-fluorouridine," J. Med. Chem., (1984), 27(4):440-444.
International Preliminary Examination Report of PCT/EP2006/069060 mailed Nov. 5, 2008.
International Preliminary Examination Report of PCT/US2004/012472 issued Dec. 1, 2005.
International Preliminary Examination Report of PCT/US2005/025916 issued Jan. 23, 2007.
International Preliminary Examination Report of PCT/US2005/032406 issued Mar. 10, 2009.
International Preliminary Examination Report of PCT/US2008/058183 issued Apr. 7, 2010.
International Search Report and Written Opinion of PCT/US2009/069475 mailed May 10, 2010.
International Search Report of International Application No. PCT/US05/25916 mailed Jun. 15, 2006.
International Search Report of PCT/EP2006/069060 (WO2007/065829) mailed Jan. 30, 2007.
International Search Report of PCT/US2004/012472 (WO2005/003147) mailed Dec. 30, 2004.
International Search Report of PCT/US2005/032406 (WO2006/031725) mailed May 8, 2008.
International Search Report of PCT/US2008/058183 (WO2008/121634) mailed Mar. 31, 2010.
International Search Report of PCT/US2009/046619 (WO/2009/152095) mailed Sep. 23, 2010.
International Search Report of PCT/US2010/035641 mailed Sep. 28, 2010.
Ishii, et al., "Expression of Hepatitis C Virus NS5B Protein: Characterization of Its RNA Polymerase Activity and RNA Binding," Hepatology, (1999), 29:1227-1235.
Iyer, et al., "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)" J. Med. Chem., (2000), 43:2266-2274.
Jin, et al., "Expression, Isolation, and Characterization of the Hepatitis C Virus ATPase/RNA Helicase," Arch. Biochem. Biophys., (1995), 323(1):47-53.
Jones, et al., "Minireview: nucleotide prodrugs," Antiviral Research, (1995), 27:1-17.
Juodka, et al., "Oligonucleotides and nucleotide-peptides. XXXIV. Synthesis and some properties of complex nucleotidyl (oligonucleotidyl)-P—N)-amino acids (peptides) and their ethyl esters," J. Carbohydrates, Nucleosides, Nucleotides, (1979), 6(4):333-357.
Juodka, et al., "Oligonucleotides and nucleotide-peptides. XXXV. Some properties of nucleotidyl(5' →N)-amino acids esters differing in amino acid and nucleotide components," J. Carbohydrates, Nucleosides, Nucleotides, (1981), 8(1):19-39.
Juodka, et al., "Oligonucleotides and nucleotide-peptides. XXXVII. On the mechanism of hydrolysis of uridylyl-(5' →N)-amino acids. Intramolecular catalysis by the α-carboxyl group of amino acids," J. Carbohydrates, Nucleosides, Nucleotides, (1981), 8(6):519-535.
Khamnei et al., "Neighboring Group Catalysis in the Design of Nucleotide Prodrugs," J. Med. Chem., (1996), 39:4109-4115.
Kim, et al., "C-Terminal domain of the hepatitis C virus NS3 protein contains an RNA helicse activity," Biochem. Biophys. Res. Comm., (1995), 215(1):160-166.
Kim, et al., "Monitoring the Intracellular Metabolism of Nucleoside Phosphoramidate Pronucleotides by 31P NMR," Nucleosides, Nucleotides and Nucleic Acids, (2004), 23(1):483-493.
Koonin, et al., "Evolution and Taxonomy of Positive-Strand RNA Viruses: Implications of Comparative Analysis of Amino Acid Sequences," Crir. Rev. Biochem. Molec. Biol., (1993), 28(5):375430.
Kotra, et al., "Structure-Activity Relationships of 2'-Deoxy-2',2'-difluoro-L-erythro-pentofuranosyl Nucleosides," J. Med. Chem., (1997), 40:3635-3644.
Kryuchkov, et al., "Influence of Solvent on the Strength of Cyclic Oxygen-Containing Phosphorus Acids," Bulletin of the Academy of Sciences of the USSR. Division of Chemical Science, (1987), 36(6 Part 1):1145-1148.
Kucera, et al., "Novel Membrane-Interactive Ether Lipid Analogs That Inhibit Infectious HIV-1 Production and Induce Defective Virus Formation," AIDS Research and Human Retroviruses, (1990), 6(4):491-501.
Lackey, et al., "Enzyme-catalyzed therapeutic agent (ECTA) design: activation of the antitumor ECTA compound NB1011 by thymidylate synthase," Biochemical Pharmacology, (2001), 61:179-189.
Lehsten, et al., "An Improved Procedure for the Synthesis of Nucleoside Phosphoramidates," Organic Process Research and Development, (2002), 6:819-822.
Li, et al., "Synthesis of the Phosphoramidite Derivative of 2'-Deoxy-2'-C-Beta-methylcytidine", J. Org. Chem., (2003), 68:6799-6802.

(56) References Cited

OTHER PUBLICATIONS

Lochmann, et al., "Biochemical Properties of Hepatitis C Virus NS5B RNA-Dependent RNA Polymerase and Identification of Amino Acid Sequence Motifs Essential for Enzymatic Activity," J. Virol., (1997), 71(11):8416-8428.

Lohmann, et al., Biochemical and Kinetic Analyses of NS5B RNA-Dependent RNA Polymerase of the Hepatitis C Virus, Virology, (1998), 249:108-118.

Lopez Aparicio, et al., "Synthesis of Saccharinic Acid Derivatives, Branched-Chain Sugars, Part VII," Carbohydrate Research, (1984), 129:99-109.

McGuigan, et al., " Application of Phosphoramidate ProTide Technology Significantly Improves Antiviral Potency of Carbocyclic Adenosine Derivatives," J. Med. Chem., (2006), 49:7215-7226.

McGuigan, et al., "Application of Phosphoramidate Pronucleotides Technology to Abacavir Leads to a Significant Enhancement of Antiviral Potency," J. Med. Chem., (2005), 48:3504-3515.

McGuigan, et al., "Aryl phosphate derivatives of AZT retain activity against HIV1 in cell lines which are resistant to the action of AZT," Antiviral Research, (1992), 17:311-321.

McGuigan, et al., "Aryl Phosphoramidate Derivatives of d4T Have Improved Anti-HIV Efficacy in Tissue Culture and May Act by the Generation of a Novel Intracellular Metabolite," J. Med. Chem., (1996), 39:1748-1753.

McGuigan, et al., "Synthesis and anti-HIV activity of some novel chain-extended phosphoramidate derivatives of d4T (stavudine): esterase hydrolysis as a rapid predictive test for antiviral potency," Antiviral Chemistry and Chemotherapy, (1998), 9:109-115.

McGuigan, et al., "Synthesis and evaluation of some novel phosphoramidate derivatives of 3'-azido-3'-deoxythymidine (AZT) as anti-HIV compounds," Antiviral Chemistry and Chemotherapy, (1990), 1(2):107-113.

McIntee, et al., "Amino Acid Phosphoramidate Nucleosides: Potential ADEPT/GDEPT Substrates," Biorg. & Med. Chem. Lett., (2001), 11:2803-2805.

McIntee, et al., "Probing the Mechanism of Action and Decomposition of Amino Acid Phosphomonoester Amidates of Antiviral Nucleoside Prodrugs," J. Med. Chem., (1997), 40:3323-3331.

Meire, et al., "Cyclic Saligenyl Phosphotriesters of 2',3'-Dideoxy-2',3'-didehydrothymidine (d4T)—A New Pro-Nucleotide Approach," Bioorganic & Medicinal Chemistry Letters, (1997), 7(2):99-104.

Meyers, et al., "Moelcular Characterization of Pestiviruses," Advances in Virus Research, (1996), 47:53-118.

Mitchell, et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. 1, (1992), 18:2345-2353.

Moennig, et al., "The Pestiviruses," Adv. Vir. Res., (1992), 41:53-98.

Monath, et al., "Effect of recombinant human granulocyte-macrophage colony-stimulating factor on chemotherapy-induced myelosuppression," New Eng. J. Med, (1988), 319(10):641-643.

Morissette, et al., "High-throughput crystallization: polymorphs, salts, co-crystals and solvates of pharmaceutical solids," Adv. Drug Delivery Rev., (2004), 56:275-300.

Neidlein, et al., "Mild preparation of 1-benzyloxyiminoalkylphosphonic dichlorides: Aplication to the synthesis of cyclic phosphonic diesters and cyclic monoester amides," Heterocycles, (1993), 35(2):1185-1203.

Nelson, et al., "The Question fo Chair-Twist Equilibria for the Phosphate Rings of Nucleoside Cyclic 3',5'-Monophosphates. 1H NMR and X-ray Crystallographic Study of the Diastereomers of Thymidine Phenyl Cyclic 3',5'-Monophosphate," J. Am. Chem. Soc., (1987), 109(13):4058-4064.

Ni, et al., "Progress and development of small molecule HCV antivirals," Current Opinion in Drug Discovery and Development, (2004), 7(4):446-459.

Nifantyev, et al., "Synthesis and Structure of Some Stable Phospholane-Phospholanes," Phosphorus, Sulfur, and Silicon (1996), 113:1-13.

Novak, et al., "Chiroptical Properties of 2-Methyl-1,4-Lactones; Revised Absolute Configuration of 2-Deoxy-2-C-Methyl-erythro-D-Pentono-1,4-Lactones," Collection of Czechoslovak Chemical Communications, (1974), 39:869-882.

Novak, et al., "Nucleic Acid Components and Their Analogues. CXLIII. Nucleosides Derived From 2-Deoxy-2(R)-C-Methyl-erythro-D-Pentose," Collection of Czechoslovak Chemical Communications, (1971), 36:3670-3677 1971.

Oishi, et al., "Asymetric Dihydroxylation of Chiral Olefins. High Control of Diastereofacial Selection," Tetrahedron Letters, (1993), 34(22):3573-3576.

Olsen, et al., "2'-Modified Nucleoside Analogs as Inhibitors of Hepatitis C RNA Replication," (Oral Session V: Hepatitis C Virus, Flaviviruses), 16th International Conference on Antiviral Research, Abstract No. 121, p. A76 (Apr. 27-May 1, 2003, Savannah, GA)).

Otto, M.J. "Evaluation of Nucleoside Analogs in the Hepatitis C Virus Replicon System," Framing the Knowledge of Therapeutics for Viral Hepatitis Ed. By RF Schinazi and ER Schiff., (2006), 247-261.

Partial International Search Report of PCT/US2009/069475 (WO/2010/075554) mailed Mar. 5, 2010.

Perrone, et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," J. Med. Chem., (2007), 50:5463-5470.

Piantadosi, et al., "Synthesis and Evaluation of Novel Ether Lipid Nucleoside Conjugates for Anti-HIV-I Activity,", J. Med. Chem., (1991), 34(4):1408-1414.

Pierra, et al., "Synthesis and Pharmacokinetics of Valopicitabine (NM283), an Efficient Prodrug of the Potent Anti-HCV Agent 2'-C-Methylcytidine," J. Med. Chem., (2006), 49(22):6614-6620.

Pogam, et al., "No Evidence of R7128 Drug Resistance After Up to 4 Weeks Treatment of GT I, 2 and 3 Hepatitis C Virus Infected Individuals", from 44th Annual Meeting of European Association for the Study of the Liver (EASL), Copenhagen, Denmark Apr. 22 - Apr. 26, 2009.

Remy, et al., "Studies on Fluorinated Pyrimidines. XIV. The Synthesis of Derivatives of 5-Fluoro-2'deoxyuridine 5'-Phosphate and Related Compounds," J. Org. Chem., (1962), 27:2491-2500.

Saboularda, et al., "Characterization of the Activation Pathway of phosphoramidate Triester Prodrugs of Stavudine and Zidovudine," Molecular Pharmacoogy, (1999), 56:693-704.

Schultz, et al., "Prodrugs of Biologically Active Phosphate Esters," Bioorganic & Medicinal Chemistry, (2003), 11:885-898.

Shih, et al., "Preparation and Structure of 2-Dimethylamino-4-pheny1-1,3,2-dioxaphosphorinane-2- oxides," Bull. Inst. Chern., Academia Sinica, (1994), 41:9-16.

Siccardi, et al., "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers," The Journal of Phannacology and Experimental Therapeutics, (2003), 307(3):1112-1119.

Siccardi, et al., "Stereospecific chemical and enzymatic stability of phosphoramidate triester prodrugs of d4T in vitro," European Journal of Pharmaceutical Sciences, (2004), 22:25-31.

Siddiqui, et al., "Design and Synthesis of Lipophilic Phosphoramidate d4T-MP Prodrugs Expressing High Potency Against HIV in Cell Culture: Structural Determinants for in Vitro Activity and QSAR," J. Med. Chem., (1999), 42:4122-4128.

Siddiqui, et al., "Enhancing the Aqueous Solubility of d4T-based Phosphoramidate Prodrugs," Bioorganic & Medicinal Chemistry Letters, (2000), 10:381-384.

Smirnov, et al., "A fluorescent study of tryptophan derivatives of oligonucleotides and their helical complexes and polyuridylic acid," FEBS Letters, (1975), 51(1):211-214.

Sofia, et al., "R7128, A Potent and Selective Nucleoside Inhibitor of HCV NS5B Polymerase: An Overview of Clinical Efficacy and Progress Toward Second Generation Inhibitors", From CHI: HCV Drug Discovery 2008, Chicago, IL, Apr. 28, 2008.

(56) References Cited

OTHER PUBLICATIONS

Sofia, et al., "β-D-2'-Deoxy-2'-C-methyluridine Phosphoramidates: Potent and Selective Inhibitors of HCV RNA Replication", Poster #P-259, Presented at the 14th International Symposium on Hepatitis C Virus and Related Viruses, Glasgow, Scotland, UK, Sep. 9-13, 2007.
Sofia, et al., "β-D-2'-Deoxy-2'-fluoro-2'-C-methyluridine Phosphoramidates: Potent and Selective Inhibitors of HCV RNA Replication", 2nd International Workshop on HCV, Poster #7, 2007.
Sofia, M.J., "Discovery of PSI-352938 and PSI-353661: Purine Nucleotide Prodrugs for the Treatment of HCV," First Disclosure Symposium, ACS 240th National Meeting, Boston, MA, Aug. 2010.
Sofia, M.J., "β-D-2'-Deoxy-2'-fluoro-2'-C-methyluridine Phosphoramidates: Potent and Selective Inhibitors of HCV RNA Replication", 2nd International Workshop on HCV—Resistance and New Compounds, Oct. 31, 2007.
Song, et al., "Pharmacokinetics of Amino Acid Phosphoramidate Monoesters of Zidovudine in Rats," Antimicrobial Agents and Chemotherapy, (2002), 4(5):1357-1363.
Starrett, et al., "Synthesis, Oral Bioavailability Determination, and in Vitro Evaluation of Prodrugs of the Antiviral Agent 9-[2-(Phosphonomethoxy)ethyl]adenine (PMEA)," J. Med. Chem., (1994), 37(12):1857-1864.
Stella, V.J., "Prodrugs as Therapeutics," Expert Opinion Ther. Patents, (2004), 14(3):277-280.
Stuyver, et al., "Dynamics of Subgenomic Hepatitis C Virus Replicon RNA Levels in Huh-7 Cells after exposure to Nucleoside Antimetabolites," Journal of Virology, (Oct. 2003), 77(19):10689-10694 (Oct. 2003).
Stuyver, et al., "Inhibition of hepatitis C replicon RNA synthesis by Beta-D-2'-deoxy-2'-fluoro-2'C-methlcytidine: a specific inhibitor of hepatitis C virus replication," Antiviral Chemistry & Chemotherapy, (2006), 17:79-87.
Stuyver, et al., "Ribonucleoside Analogue that Blocks Replication of Bovine Viral Diarrhea and Hepatitis C Viruses in Culture," Antimicrob. Agents Chemother., (Jan. 2003), 47(1):244-254.
Sun, et al., "Study on the Chirality of Sulfur in Ethyl (2S,3R,4R)-4,5-O-lsopropylidene-2,3-sulfinyl- 2,3,4,5-tetrahydroxy-pentanoate", Acta Chimica Sinica, (1997), 55:600-604.
Sun, et al., "The Synthesis of(2s,3R)-Sphingosine from D-Mannitol," Acta Chimica Sinica, (1996), 54:826-832.
Supplemental European Search Report of European Patent Appln No. EP 05775359.2 dated Sep. 15, 2010.
Tan, et al., "Hepatitis C Therapeutics: Current Status and Emerging Strategies," Nature Rev. Drug Discov., (2002), 1:867-881.
Tomei, et al., "NS3 Is a Serine Protease Required for Processing of Hepatitis C Virus Polyprotein," J. Viral., (1993), 67(7):4017-4026.
Uckun, et al., "In Vivo pharmacokinetics and Toxicity Profile of the Anti-HIV Agent Stampidine in Dogs and Feline Immunodeficiency Virus-infected Cats," Arzneim.-Forsch./Drug Res., (2006), 56(2a):176-192.
Valette, et al., "Decomposition Pathways and in Vitro HIV Inhibitory Effects of IsoddA Pronucleotides: Toward a Rational Approach for Intracellular Delivery of Nucleoside 5' - Monophosphates," J. Med. Chem., (1996), 39:1981-1990.
Venkatachalam, et al., "Rational Drug Design of Multifunctional Phosphoramidate Substituted Nucleoside Analogs," Current Pharmaceutical Design, (2004), 10:1713-1726.
Venkatachalam, et al., "Synthesis and metabolism of naphthyl substituted phosphoramidate derivatives of stavudine," Bioorganic & Medicinal Chemistry, (2006), 14:5161-5177.
Wagner, et al., "Antiviral Nucleoside Drug Delivery via Amino Acid Phosphoramidates," Nucleosides, Nucleotides and Nucleic Acids, (1999), 18(4):913-919.
Walker, et al., "Promising candidates for the treatment of chronic hepatitis C," Exp. Opin. Investig. Drugs, (2003), 12(8):1269-1280.
Warrener, et al., "Pestivirus NS3 (p80) Protein Possesses RNA Helicse Activity," J. Viral., (1995), 69(3):1720-1726.
Wiskerchen, et al,. "Pestivirus Gene Expression: Protein p80 of Bovine Viral Diarrhea Virus Is a Proteinase Involved in Polyprotein Processing," Virology, (1991), 184:341-350.
Wolff, M.E., "Burger's Medicinal Chemistry and Drug Discovery, 5ed, Part I", John Wiley & Sons, (1995), 975-977.
Written Opinion of PCT/EP2006/069060 mailed Jan. 30, 2007.
Written Opinion of PCT/US2004/012472 mailed Dec. 30, 2004.
Written Opinion of PCT/US2005/025916 mailed Jun. 15, 2006.
Written Opinion of PCT/US2005/032406 mailed May 8, 2008.
Written Opinion of PCT/US2008/058183 mailed Mar. 31, 2010.
Written Opinion of PCT/US2010/035641 mailed Sep. 28, 2010.
Wu, et al., "Synthesis and Biological Activity of a Gemcitabine Phosphoramidate Prodrug," J. Med. Chem., (2007), 50:3743-3746.
Wu, et al., "Trageting NS5B RNA-Dependent RNA Polymerase for Anti-HCV Chemotherapy," Current Drug Targets-Infectious Disorders, (2003), 3:207-219.
Xu, et al., "Bovine Viral Diarrhea Virus NS3 Serine Proteinase: Polyprotein Cleavage Sites, Cofactor Requirements, and Molecular Model of an Enzyme Essential for Pestivirus Replication," J. Virol., (1997), 71(7):5312-5322.
Yuan, et al., "Expression, Purification, and Partial Characterization of HCV RNA Polymerase," Biochem. Biophys. Res. Comm., (1997), 232:231-235.
Yuodka, et al., "Oligonucleotides and polynucleotides. XXVI. Synthesis of esters of nucleotidyl—and oligonucleotidyl-(5' →N)-(amino acid)s and peptides," translated from Bioorganicheskaya Khimiya, (1976), 2(11):1513-1519.
Zhong, et al., "Identification and Characterization of an RNA-Dependent RNA Polymerase Activity within the Nonstructural Protein 5B Region of Bovine Viral Diarrhea Virus," J. Viral., (1998), 72(11):9365-9369.
Zon, G., "Cyclophosphamide Analogues," Progress in Medicinal Chemistry, (1982), 19:205-246.
Office Actions issued and Responses submitted in U.S. Appl. No. 12/053,015 on PAIR.
Office Actions issued and Responses submitted in U.S. Appl. No. 12/142,536 on PAIR.
Office Actions issued and Responses submitted in U.S. Appl. No. 12/142,554 on PAIR.
Office Actions issued and Responses submitted in U.S. Appl. No. 12/131,868 on PAIR.
Office Actions issued and Responses submitted in U.S. Appl. No. 12/553,483 on PAIR.
Office Actions issued and Responses submitted in U.S. Appl. No. 12/240,342 on PAIR.
Office Actions issued and Responses submitted in U.S. Appl. No. 12/479,075 on PAIR.
Office Actions issued and Responses submitted in U.S. Appl. No. 12/654,821 on PAIR.
Office Actions issued and Responses submitted in U.S. Appl. No. 12/645,710, on PAIR.
Office Actions issued and Responses submitted in U.S. Appl. No. 12/645,765, on PAIR.
Office Actions issued and Responses submitted in U.S. Appl. No. 12/783,680, on PAIR.
Office Action and Responses submitted in U.S. Appl. No. 11/353,597 on PAIR.
Office Action and Responses for U.S. Appl. No. 11/225,425 on PAIR.
Office Action and Responses submitted in U.S. Appl. No. 11/635,898 on PAIR.
Office Action and Responses submitted in U.S. Appl. No. 10/828,753 on PAIR.
Office Action and Responses submitted in U.S. Appl. No. 13/439,991 on PAIR.
Valette et al., "Decomposition Pathways and in Vitro HIV Inhibitory Effects of IsoddA Pronucleotides: Toward a Rational Approach for Intracellular Delivery of Nucleoside 5'-Monophosphates" Journal of Medicinal Chemistry, 1996, 39, 1981-1990.
Babu BR, et al. 2'-Spiro ribo- and arabinonucleosides: synthesis, molecular modelling and incorporation into oligodeoxynucleotides. Org Biomol Chem. 2003 Oct 21;1(20):3514-26.

(56) References Cited

OTHER PUBLICATIONS

Chang, et al. Discovery of Psi-353661, a Novel Purine Nucleotide Prodrug for the Treatment of HCV Infection. ACS Medicinal Chemistry Letters (2011), 2(2), 130-135.

Reddy, et al. Stereoselective Synthesis of PSI-352938: A βD-20-Deoxy-20-r-fluoro-20-β-C-methyl-30,50-cyclic Phosphate Nucleotide Prodrug for the Treatment of HCV. Journal of Organic Chemistry (2011), 76(10), 3782-3790.

Ross, et al. Synthesis of Diastereomerically Pure Nucleotide Phosphoramidates. Journal of Organic Chemistry (2011), 76(20), 8311-8319.

International Search Report of PCT/US2011/062643 (WO2012/075140) mailed May 10, 2012.

\* cited by examiner

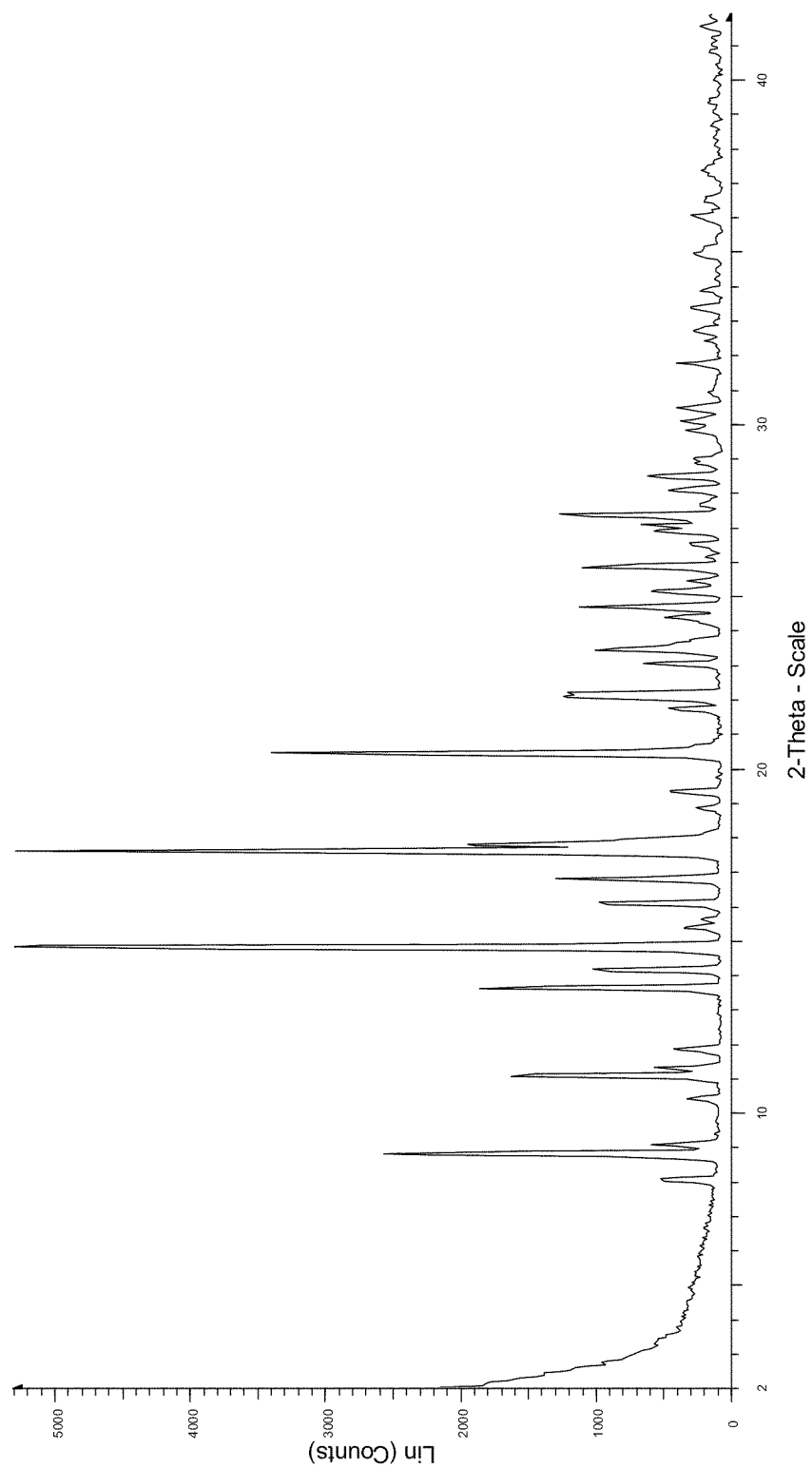
Figure 1. High resolution XRPD of 1·H₂O

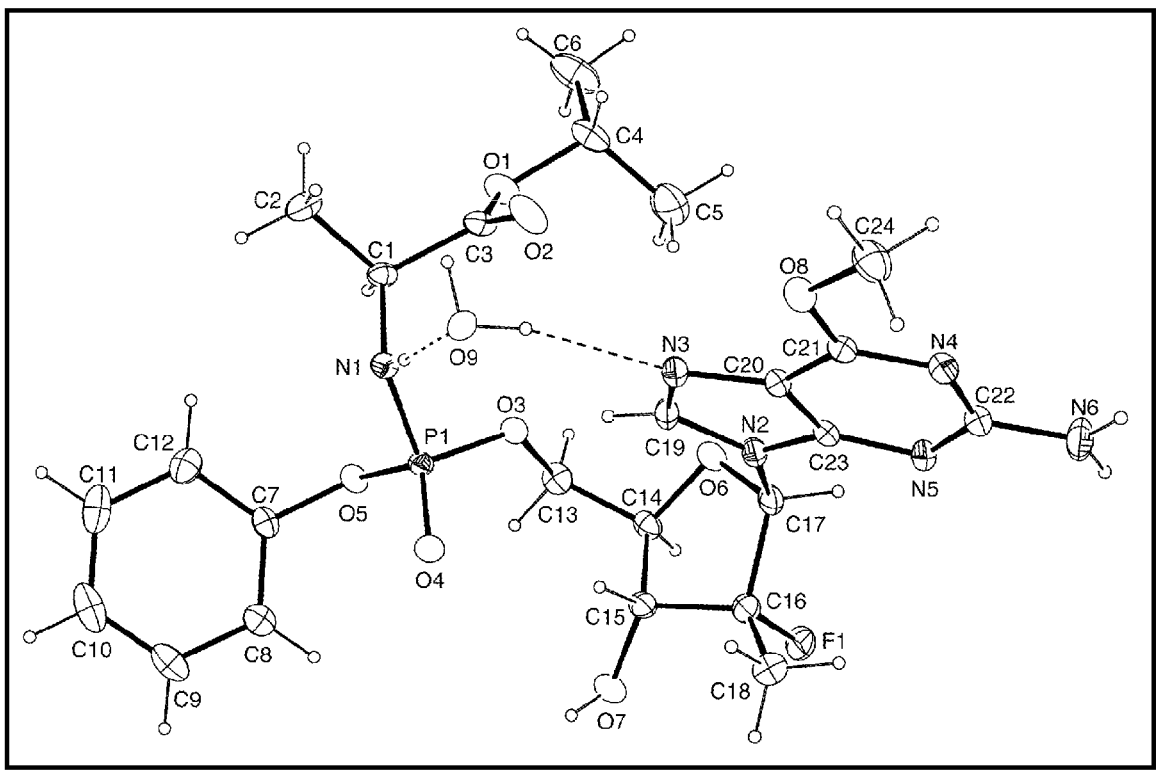
Fig 2. ORTEP drawing of 1·H$_2$O with 30% probability thermal ellipsoids

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: HCV Sense Primer

<400> SEQUENCE: 1
agccatggcg ttagtatgag tgt                                            23

<210> SEQ ID NO 2
<211> LENGTH: 18
<212> TYPE: DNA
<213> ORGANISM: Artificial Sequence
<220> FEATURE:
<223> OTHER INFORMATION: HCV Antisense Primer

<400> SEQUENCE: 2
ttccgcagac cactatgg                                                  18

<210> SEQ ID NO 3
<211> LENGTH: 20
<212> TYPE: DNA
<213> ORGANISM: Artificial Sequence
```

```
<220> FEATURE:
<223> OTHER INFORMATION: HCV Probe with 5'-FAM and 3'-TAMRA Labels

<400> SEQUENCE: 3
cctccaggac cccccctccc                                              20
```

PURINE NUCLEOSIDE PHOSPHORAMIDATE

PRIORITY

This application claims priority to U.S. 61/319,513, filed on Mar. 31, 2010; U.S. 61/319,548, filed on Mar. 31, 2010; and U.S. 61/355,940, filed on Jun. 17, 2010, the subject matter of which is incorporated by reference in its entirety.

FIELD OF THE INVENTION

Disclosed herein are nucleoside phosphoramidates and their use as agents for treating viral diseases. These compounds are inhibitors of RNA-dependent RNA viral replication and are useful as inhibitors of HCV NS5B polymerase, as inhibitors of HCV replication and for treatment of hepatitis C infection in mammals.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al, *Heptology*, 1999, 29: 1227-1235; V. Lohmann, et al., *Virology*, 1998, 249: 108-118). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Flaviviridae Viruses

The Flaviviridae family of viruses comprises at least three distinct genera: pestiviruses, which cause disease in cattle and pigs; flaviviruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic Fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med*, 1988, 319, 641-643).

The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al, Adv. Vir. Res. 1992, 41, 53-98). Human pestiviruses have not been as extensively characterized as the animal pestiviruses. However, serological surveys indicate considerable pestivirus exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The hepacivirus group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al., *Nature*, 1988, 333, 22; Bazan and Fletterick *Virology*, 1989, 171, 637-639; Gorbalenya et al., *Nucleic Acid Res.*, 1989, 17, 3889-3897). Similarly, the NS5B proteins of pestiviruses and hepaciviruses have the motifs characteristic of RNA-directed RNA polymerases (Koonin, E. V. and Dolja, V. V., *Crir. Rev. Biochem. Molec. Biol.* 1993, 28, 375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett, *Virology,* 1991, 184, 341-350; Bartenschlager et al., *J. Virol.* 1993, 67, 3835-3844; Eckart et al. *Biochem. Biophys. Res. Comm.* 1993, 192, 399-406; Grakoui et al., *J. Virol.* 1993, 67, 2832-2843; Grakoui et al., *Proc. Natl. Acad. Sci. USA* 1993, 90, 10583-10587; Hijikata et al., *J. Virol.* 1993, 67, 4665-4675; Tome et al., *J. Virol.,* 1993, 67, 4017-4026). The NS4A protein, in both cases, acts as a cofactor with the NS3 serine protease (Bartenschlager et al., *J. Virol.* 1994, 68, 5045-5055; Failla et al., *J. Virol.* 1994, 68, 3753-3760; Xu et al., *J. Virol.,* 1997, 71:53 12-5322). The NS3 protein of both viruses also functions as a helicase (Kim et al., *Biochem. Biophys. Res. Comm.,* 1995, 215, 160-166; Jin and Peterson, *Arch. Biochem. Biophys.,* 1995, 323, 47-53; Warrener and Collett, *J. Virol.* 1995, 69, 1720-1726). Finally, the NS5B proteins of pestiviruses and hepaciviruses have the predicted RNA-directed RNA polymerases activity (Behrens et al., EMBO, 1996, 15, 12-22; Lechmann et al., *J. Virol.,* 1997, 71, 8416-8428; Yuan et al., *Biochem. Biophys. Res. Comm.* 1997, 232, 231-235; Hagedorn, PCT WO 97/12033; Zhong et al, *J. Virol.,* 1998, 72, 9365-9369).

Currently, there are limited treatment options for individuals infected with hepatitis C virus. The current approved therapeutic option is the use of immunotherapy with recombinant interferon-α alone or in combination with the nucleoside analog ribavirin. This therapy is limited in its clinical effectiveness and only 50% of treated patients respond to therapy. Therefore, there is significant need for more effective and novel therapies to address the unmet medical need posed by HCV infection.

A number of potential molecular targets for drug development of direct acting antivirals as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Inhibitors of HCV NS5B as potential therapies for HCV infection have been reviewed: Tan, S.-L., et al., *Nature Rev. Drug Discov.,* 2002, 1, 867-881; Walker, M. P. et al., *Exp. Opin. Investigational Drugs,* 2003, 12, 1269-1280; Ni, Z-J., et al., *Current Opinion in Drug Discovery and Development,* 2004, 7, 446-459; Beaulieu, P. L., et al., *Current Opinion in Investigational Drugs,* 2004, 5, 838-850; Wu, J., et al., *Current Drug Targets-Infectious Disorders,* 2003, 3, 207-219; Griffith, R. C., et al, *Annual Reports in Medicinal Chemistry,* 2004, 39, 223-237; Carrol, S., et al., *Infectious Disorders-Drug Targets,* 2006, 6, 17-29. The potential for the emergence of resistant HCV strains and the need to identify agents with broad genotype coverage supports the need for continuing efforts to identify novel and more effective nucleosides as HCV NS5B inhibitors.

Nucleoside inhibitors of NS5B polymerase can act either as a non-natural substrate that results in chain termination or as a competitive inhibitor which competes with nucleotide binding to the polymerase. To function as a chain terminator the nucleoside analog must be taken up by the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. Unfortunately, this limits the direct evaluation of nucleosides as inhibitors of HCV replication to cell-based assays capable of in situ phosphorylation.

In some cases, the biological activity of a nucleoside is hampered by its poor substrate characteristics for one or more of the kinases needed to convert it to the active triphosphate form. Formation of the monophosphate by a nucleoside kinase is generally viewed as the rate limiting step of the three phosphorylation events. To circumvent the need for the initial phosphorylation step in the metabolism of a nucleoside to the active triphosphate analog, the preparation of stable phosphate prodrugs has been reported. Nucleoside phosphoramidate prodrugs have been shown to be precursors of the active nucleoside triphosphate and to inhibit viral replication when administered to viral infected whole cells (McGuigan, C., et al., *J. Med. Chem.,* 1996, 39, 1748-1753; Valette, G., et al., *J. Med. Chem.,* 1996, 39, 1981-1990; Balzarini, J., et al., *Proc. National Acad Sci USA,* 1996, 93, 7295-7299; Siddiqui, A. Q., et al., *J. Med. Chem.,* 1999, 42, 4122-4128; Eisenberg, E. J., et al., *Nucleosides, Nucleotides and Nucleic Acids,* 2001, 20, 1091-1098; Lee, W. A., et al., *Antimicrobial Agents and Chemotherapy,* 2005, 49, 1898); US 2006/0241064; and WO 2007/095269.

Also limiting the utility of nucleosides as viable therapeutic agents is their sometimes poor physicochemical and pharmacokinetic properties. These poor properties can limit the intestinal absorption of an agent and limit uptake into the target tissue or cell. To improve on their properties prodrugs of nucleosides have been employed. It has been demonstrated that preparation of nucleoside phosphoramidates improves the systemic absorption of a nucleoside and furthermore, the phosphoramidate moiety of these "pronucleotides" is masked with neutral lipophilic groups to obtain a suitable partition coefficient to optimize uptake and transport into the cell dramatically enhancing the intracellular concentration of the nucleoside monophosphate analog relative to administering the parent nucleoside alone. Enzyme-mediated hydrolysis of the phosphate ester moiety produces a nucleoside monophosphate wherein the rate limiting initial phosphorylation is unnecessary. To this end, U.S. patent application Ser. No. 12/053,015, which corresponds to WO 2008/121634 and US 2010/0016251, discloses a number of phosphoramidate nucleoside prodrugs, many of which show activity in an HCV assay. Several compounds disclosed in US 2010/0016251 were tested as a potential clinical candidate for approval by the FDA.

SUMMARY OF THE INVENTION

Disclosed herein is a compound represented by formula 1 its hydrate or solvate thereof in crystalline or crystal-like form.

1

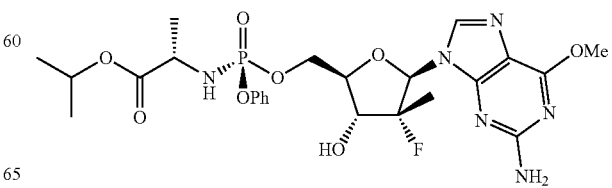

BRIEF DESCRIPTION OF THE DRAWINGS

FIG. 1. High resolution XRD diffractogram of 1.H$_2$O.
FIG. 2. X-Ray Crystal Structure for 1.H$_2$O.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "P*" (where used) means that the phosphorus atom is chiral and that it has a corresponding Cahn-Ingold-Prelog designation of "R" or "S" which have their accepted plain meanings. Due to the chirality at phosphorus, Compound 1, as used herein, is sometime referred to the S$_P$-isomer. Its diastereomeric analog is some times referred to as the R$_P$-isomer. Mixtures of the S$_P$-isomer and R$_P$-isomer are sometimes referred to as a mixture containing 1 and the R$_P$-isomer.

The term "purified," as described herein, refers to the purity of a given compound. For example, a compound is "purified" when the given compound is a major component of the composition, i.e., at least 50% w/w pure. Thus, "purified" embraces at least 50% w/w purity, at least 60% w/w purity, at least 70% purity, at least 80% purity, at least 85% purity, at least 90% purity, at least 92% purity, at least 94% purity, at least 96% purity, at least 97% purity, at least 98% purity, at least 99% purity, at least 99.5% purity, and at least 99.9% purity, wherein "substantially pure" embraces at least 97% purity, at least 98% purity, at least 99% purity, at least 99.5% purity, and at least 99.9% purity The term "about" (also represented by ~) means that the recited numerical value is part of a range that varies within standard experimental error.

The expression "substantially as shown in . . . " a specified XRPD pattern means that the peak positions shown in the XRPD pattern are substantially the same, within visual inspection or resort to selected peak listings (±0.2°2θ). One of ordinary skill understands that the intensities can vary depending on the sample.

The term "substantially anhydrous" means that a substance contains at most 10% by weight of water, preferably at most 1% by weight of water, more preferably at most 0.5% by weight of water, and most preferably at most 0.1% by weight of water.

A solvent or anti-solvent (as used in reactions, crystallization, etc. or lattice and/or adsorbed solvents) includes at least one of a C$_1$ to C$_8$ alcohol, a C$_2$ to C$_8$ ether, a C$_3$ to C$_7$ ketone, a C$_3$ to C$_7$ ester, a C$_1$ to C$_2$ chlorocarbon, a C$_2$ to C$_7$ nitrile, a miscellaneous solvent, a C$_5$ to C$_{12}$ saturated hydrocarbon, and a C$_6$ to C$_{12}$ aromatic hydrocarbon.

The C$_1$ to C$_8$ alcohol refers to a straight/branched and/or cyclic/acyclic alcohol having such number of carbons. The C$_1$ to C$_8$ alcohol includes, but is not limited to, methanol, ethanol, n-propanol, isopropanol, isobutanol, hexanol, and cyclohexanol.

The C$_2$ to C$_8$ ether refers to a straight/branched and/or cyclic/acyclic ether having such number of carbons. The C$_2$ to C$_8$ ether includes, but is not limited to, dimethyl ether, diethyl ether, di-isopropyl ether, di-n-butyl ether, methyl-t-butyl ether (MTBE), tetrahydrofuran, and dioxane The C$_3$ to C$_7$ ketone refers to a straight/branched and/or cyclic/acyclic ketone having such number of carbons. The C$_3$ to C$_7$ ketone includes, but is not limited to, acetone, methyl ethyl ketone, propanone, butanone, methyl isobutyl ketone, methyl butyl ketone, and cyclohexanone.

The C$_3$ to C$_7$ ester refers to a straight/branched and/or cyclic/acyclic ester having such number of carbons. The C$_3$ to C$_7$ ester includes, but is not limited to, ethyl acetate, propyl acetate, i-propyl acetate, n-butyl acetate, etc.

The C$_1$ to C$_2$ chlorocarbon refers to a chlorocarbon having such number of carbons. The C$_1$ to C$_2$ chlorocarbon includes, but is not limited to, chloroform, methylene chloride (DCM), carbon tetrachloride, 1,2-dichloroethane, and tetrachloroethane.

A C$_2$ to C$_7$ nitrile refers to a nitrile have such number of carbons. The C$_2$ to C$_7$ nitrile includes, but is not limited to, acetonitrile, propionitrile, etc.

A miscellaneous solvent refers to a solvent commonly employed in organic chemistry, which includes, but is not limited to, diethylene glycol, diglyme (diethylene glycol dimethyl ether), 1,2-dimethoxy-ethane, dimethylformamide, dimethylsulfoxide, ethylene glycol, glycerin, hexamethylphsphoramide, hexamethylphosphorous triame, N-methyl-2-pyrrolidinone, nitromethane, pyridine, triethyl amine, and acetic acid.

The term C$_5$ to C$_{12}$ saturated hydrocarbon refers to a straight/branched and/or cyclic/acyclic hydrocarbon. The C$_5$ to C$_{12}$ saturated hydrocarbon includes, but is not limited to, n-pentane, petroleum ether (ligroine), n-hexane, n-heptane, cyclohexane, and cycloheptane.

The term C$_6$ to C$_{12}$ aromatic refers to substituted and unsubstituted hydrocarbons having a phenyl group as their backbone. Preferred hydrocarbons include benzene, xylene, toluene, chlorobenzene, o-xylene, m-xylene, p-xylene, xylenes, and anisole.

The term "co-crystallates" include co-crystallates of 1 in combination with salts, which embraces pharmaceutically acceptable salts.

The term "salts," as described herein, refers to a compound comprising a cation and an anion, which can produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation. This term is meant to embrace pharmaceutically acceptable salts.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among Na$^+$, Mg$^{2+}$, Ca$^{2+}$, NH$_g$R'''$_{4-g}^+$, in which R''' is a C$_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

The term "crystalline" refers to a situation where a solid sample of 1 has crystalline characteristics when determined by X-ray powder diffraction or a single crystal X-ray technique.

The term "crystal-like" refers to a situation where a solid sample of 1 has crystalline characteristics when determined by one means, e.g., visually or by optical or polarizing microscopy, but does not have crystalline characteristics when determined by another means, e.g., x-ray powder diffraction. Methods of visually determining the crystallinity of a solid sample by visual or by optical or by polarizing microscopy are disclosed in U.S. Pat. Nos. <695> and <776>, both of which are incorporated by reference. A solid sample of 1 that is "crystal-like" may be crystalline under certain conditions but may become non-crystalline when subjected to other conditions.

The term "amorphous" refers to a situation where a solid sample of 1 is neither crystalline nor crystal-like.

Embodiments

A first embodiment is directed to a compound represented by a compound represented by formula 1 its hydrate or solvate thereof in crystalline or crystal-like form.

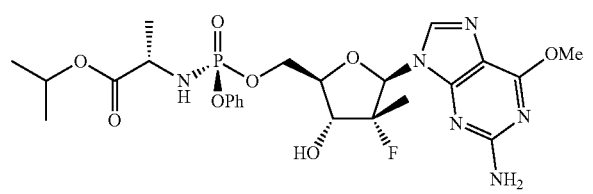

1

The compound represented by formula 1 as its hydrate in crystalline or crystal-like form is designated as 1.mH$_2$O, where m varies in an integer or non-integer amount from about 0 to about 5. The compound represented by formula 1 as its solvate in crystalline or crystal-like form is designated as 1.nS, where n varies in an integer or non-integer amount from about 0 to about 3. The compound represented by formula 1 its hydrate or solvate might have a certain advantageous amount of adsorbed solvent (S) or water. In which case, the amount of S or water can vary from about 0 wt. % to about 10 wt. % based on the weight of the compound represented by formula 1 or its hydrate in crystalline or crystal-like form.

A second embodiment is directed to crystalline or crystal-like 1.

A third embodiment is directed to crystalline or crystal-like 1.mH$_2$O, where m varies in an integer or non-integer amount from about 0 to about 5.

A first aspect of the third embodiment is directed to crystalline or crystal-like 1.H$_2$O.

A second aspect of the third embodiment is directed to crystalline or crystal-like 1.½H$_2$O.

A fourth embodiment is directed to crystalline 1.H$_2$O.

A first aspect of the fourth embodiment is directed to an orthorhombic crystalline 1.H$_2$O, preferably having the following unit cell parameters a ~10.99 Å, b ~13.09 Å, and c ~20.36 Å.

A second aspect of the fourth embodiment is directed to a crystalline 1.H$_2$O having an XRPD 2θ-reflection (°) at about: 14.8.

A third aspect of the fourth embodiment is directed to a crystalline 1.H$_2$O having XRPD 2θ-reflections (°) at about: 14.8 and 17.6

A fourth aspect of the fourth embodiment is directed to a crystalline 1.H$_2$O having XRPD 2θ-reflections (°) at about: 14.8, 17.6, and 20.4

A fifth aspect of the fourth embodiment is directed to a crystalline 1.H$_2$O having XRPD 2θ-reflections (°) at about: 8.7, 14.8, 17.6, and 20.4.

A sixth aspect of the fourth embodiment is directed to a crystalline 1.H$_2$O having XRPD 2θ-reflections (°) at about: 8.7, 13.6, 14.8, 17.6, and 20.4.

A seventh aspect of the fourth embodiment is directed to a crystalline 1.H$_2$O having XRPD 2θ-reflections (°) at about: 8.7, 11.1, 13.6, 14.8, 17.6, and 20.4.

An eighth aspect of the fourth embodiment is directed to a crystalline 1.H$_2$O having an XRPD diffraction pattern substantially as that shown in FIG. 1.

A fifth embodiment is directed to substantially pure crystalline 1.H$_2$O.

A sixth embodiment is directed to crystal-like 1.H$_2$O.

Dosage, Administration, and Use

A seventh embodiment is directed to a composition for the treatment and/or prophylaxis of any of the viral agents using crystalline or crystal-like 1.mH$_2$O or 1.nS. Possible viral agents include, but are not limited to: hepatitis C virus, hepatitis B virus, Hepatitis A virus, West Nile virus, yellow fever virus, dengue virus, rhinovirus, polio virus, bovine viral diarrhea virus, Japanese encephalitis virus, or those viruses belonging to the groups of Pestiviruses, hepaciviruses, or flavaviruses.

An aspect of this embodiment is directed to a composition for the treatment of any of the viral agents disclosed herein said composition comprising a pharmaceutically acceptable medium selected from among an excipient, carrier, diluent, and equivalent medium and crystalline or crystal-like 1.mH$_2$O or 1.nS, that is intended to include its hydrates, solvates, and any crystalline forms of crystalline or crystal-like 1.mH$_2$O or 1.nS.

The crystalline or crystal-like 1.mH$_2$O or 1.nS may be independently formulated in a wide variety of oral administration dosage forms and carriers. Oral administration can be in the form of tablets, coated tablets, hard and soft gelatin capsules, solutions, emulsions, syrups, or suspensions. The crystalline or crystal-like 1.mH$_2$O or 1.nS is efficacious when administered by suppository administration, among other routes of administration. The most convenient manner of administration is generally oral using a convenient daily dosing regimen which can be adjusted according to the severity of the disease and the patient's response to the antiviral medication.

The crystalline or crystal-like 1.mH$_2$O or 1.nS together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w).

The crystalline or crystal-like 1.mH$_2$O or 1.nS can be administered alone but will generally be administered in admixture with one or more suitable pharmaceutical excipients, diluents or carriers selected with regard to the intended route of administration and standard pharmaceutical practice.

Solid form preparations include, for example, powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like. Examples of solid formulations are exemplified in EP 0524579; US 2002/0142050; US 2004/0224917; US 2005/0048116; US 2005/0058710; US 2006/0034937; US 2006/0057196; US 2006/0188570; US 2007/0026073; US 2007/0059360; US 2007/0077295; US 2007/0099902; US 2008/0014228; U.S. Pat. Nos. 6,267,985; 6,294,192; 6,383,471; 6,395,300; 6,569,463; 6,635,278; 6,645,528; 6,923,988; 6,932,983; 7,060,294; and 7,462,608, each of which is incorporated by reference.

Liquid formulations also are suitable for oral administration include liquid formulation including emulsions, syrups, elixirs and aqueous suspensions. These include solid form preparations which are intended to be converted to liquid form preparations shortly before use. Examples of liquid formulation are exemplified in U.S. Pat. Nos. 3,994,974; 5,695,784; and 6,977,257. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The crystalline or crystal-like 1.mH$_2$O or 1.nS may be independently formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The crystalline or crystal-like 1.mH$_2$O or 1.nS may be independently formulated for vaginal administration. Pessaries, tampons, creams, gels, pastes, foams or sprays containing in addition to the active ingredient such carriers as are known in the art to be appropriate. Certain of these formulations may also be used in conjunction with a condom with or without a spermicidal agent.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa., which is hereby incorporated by reference. A skilled formulation scientist may modify the formulations within the teachings of the specification to provide numerous formulations for a particular route of administration without rendering compositions containing the compounds contemplated herein unstable or compromising their therapeutic activity.

Additionally, the purified crystalline or crystal-like 1.mH$_2$O or 1.nS may be independently formulated in conjunction with liposomes or micelles. As to liposomes, it is contemplated that the purified compounds can be formulated in a manner as disclosed in U.S. Pat. Nos. 4,797,285; 5,013,556; 5,077,056; 5,077,057; 5,154,930; 5,192,549; 5,213,804; 5,225,212; 5,277,914; 5,316,771; 5,376,380; 5,549,910; 5,567,434; 5,736,155; 5,827,533; 5,882,679; 5,891,468; 6,060,080; 6,132,763; 6,143,321; 6,180,134; 6,200,598; 6,214,375; 6,224,903; 6,296,870; 6,653,455; 6,680,068; 6,726,925; 7,060,689; and 7,070,801, each of which is incorporated by reference. As to micelles, it is contemplated that the purified compounds can be formulated in a manner as disclosed in U.S. Pat. Nos. 5,145,684 and 5,091,188, both of which are incorporated by reference.

The fifth embodiment is directed to a use of crystalline or crystal-like 1.mH$_2$O or 1.nS in the manufacture of a medicament for the treatment of any condition the result of an infection by any one of the following viral agents: hepatitis C virus, West Nile virus, yellow fever virus, degue virus, rhinovirus, polio virus, hepatitis A virus, bovine viral diarrhea virus and Japanese encephalitis virus.

The term "medicament" means a substance used in a method of treatment and/or prophylaxis of a subject in need thereof, wherein the substance includes, but is not limited to, a composition, a formulation, a dosage form, and the like, comprising crystalline or crystal-like 1.mH$_2$O or 1.nS. It is contemplated that crystalline or crystal-like 1.mH$_2$O or 1.nS in the manufacture of a medicament, for the treatment of any of the antiviral conditions disclosed herein, either alone or in combination with another compound disclosed herein. A medicament includes, but is not limited to, any one of the compositions contemplated by the fourth embodiment disclosed herein.

An eighth embodiment is directed to a method of treatment and/or prophylaxis in a subject in need thereof said method comprises administering a therapeutically effective amount of crystalline or crystal-like 1.mH$_2$O or 1.nS to the subject.

It is intended that a subject in need thereof is one that has any condition the result of an infection by any of the viral agents disclosed herein, which includes, but is not limited to, hepatitis C virus, West Nile virus, yellow fever virus, degue virus, rhinovirus, polio virus, hepatitis A virus, bovine viral diarrhea virus or Japanese encephalitis virus, flaviviridae viruses or pestiviruses or hepaciviruses or a viral agent causing symptoms equivalent or comparable to any of the above-listed viruses.

The term "subject" means a mammal, which includes, but is not limited to, cattle, pigs, sheep, chicken, turkey, buffalo, llama, ostrich, dogs, cats, and humans, preferably the subject is a human. It is contemplated that in the method of treating a subject thereof of the ninth embodiment can be any of the compounds contemplated herein, either alone or in combination with another compound disclosed herein.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.001 and about 10 g, including all values in between, such as 0.001, 0.0025, 0.005, 0.0075, 0.01, 0.025, 0.050, 0.075, 0.1, 0.125, 0.150, 0.175, 0.2, 0.25, 0.5, 0.75, 1, 1.5, 2, 2.5, 3, 3.5, 4, 4.5, 5, 5.5, 6, 6.5, 7, 7.5, 8, 8.5, 9, and 9.5, per day should be appropriate in monotherapy or in combination therapy. A particular daily dosage is between about 0.01 and about 1 g per day, including all incremental values of 0.01 g (i.e., 10 mg) in between, a preferred daily dosage about 0.01 and about 0.8 g per day, more preferably about 0.01 and about 0.6 g per day, and most preferably about 0.01 and about 0.25 g per day, each of which including all incremental values of 0.01 g in between. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on knowledge, experience and the disclosures of this application, to ascertain a therapeutically effective amount of the compound disclosed herein for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

A first aspect of the eighth embodiment is directed to a method of treatment and/or prophylaxis in a subject in need thereof said method comprises administering to the subject a therapeutically effective amount of a compound represented by compound 1.mH$_2$O or 1.nS and a therapeutically effective amount of another antiviral agent; wherein the administration is concurrent or alternative. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours.

Examples of "another antiviral agent" include, but are not limited to: HCV NS3 protease inhibitors (see EP 1881001, US 2003187018, US 2005267018, WO 2003006490, WO 200364456, WO 2004094452, WO 2005028502, WO 2005037214, WO 2005095403, WO 2007014920, WO 2007014921, WO 2007014922, WO 2007014925, WO 2007014926, WO 2007015824, WO 2008010921, and WO 2008010921); HCV NS5B Inhibitors (see US 2004229840, US 2005154056, US 2005-98125, US 20060194749, US 20060241064, US 20060293306, US 2006040890, US 2006040927, US 2006166964, US 2007275947, U.S. Pat. No. 6,784,166, US20072759300, WO 2002057287, WO 2002057425, WO 2003010141, WO 2003037895, WO 2003105770, WO 2004000858, WO 2004002940, WO 2004002944, WO 2004002977, WO 2004003138, WO 2004041201, WO 2004065367, WO 2004096210, WO 2005021568, WO 2005103045, WO 2005123087, WO 2006012078, WO 2006020082, WO 2006065335, WO 2006065590, WO 2006093801, WO 200702602, WO 2007039142, WO 2007039145, WO 2007076034, WO 2007088148, WO 2007092000, and WO2007095269); HCV NS4 Inhibitors (see WO 2005067900 and WO 2007070556); HCV NS5a Inhibitors (see US 2006276511, WO 2006035061, WO 2006100310, WO 2006120251, and WO 2006120252); Toll-like receptor agonists (see WO 2007093901); and other inhibitors (see WO 2000006529, WO 2003101993, WO 2004009020, WO 2004014313, WO 2004014852, and WO 2004035571); compound A (shown below and disclosed in U.S. Pat. No. 7,429,572); compound B (disclosed in US 2007/0197463); compound C (disclosed in US 2010/0081628, see also compound 19a and 19b disclosed in the same application, which are individual diastereomers of compound C); compound D (disclosed in US 2010/0016251); compound E (disclosed in U.S. Ser. No. 12/783,680, as well as Rp-4 disclosed in the same application); telaprevir (also known as VX-950, which is disclosed in US 2010/0015090); boceprevir (disclosed in US 2006/0276405); BMS-790052 (disclosed in WO 2008/021927); ITMN-191 (disclosed in US 2009/0269305 at Example 62-1); ANA-598 (shown below and identified as compound 31 in F. Ruebasam et al. Biorg. Med. Chem. Lett. (2008) 18: 3616-3621; and TMC435 (formerly known as TMC435350)

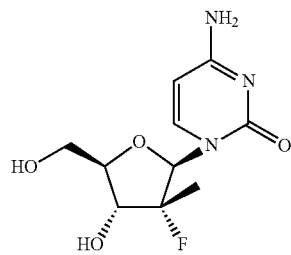

A

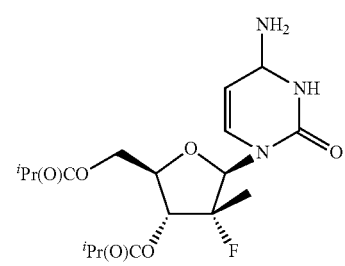

B

-continued
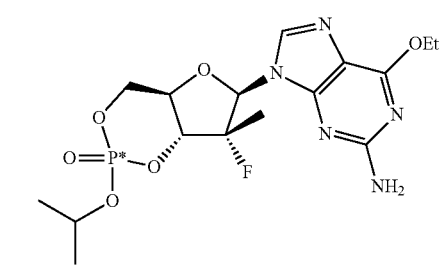
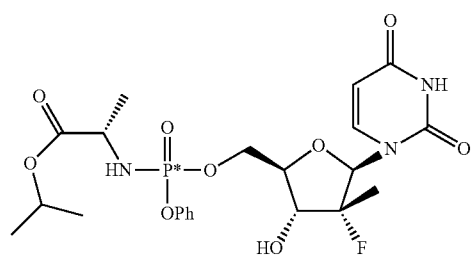
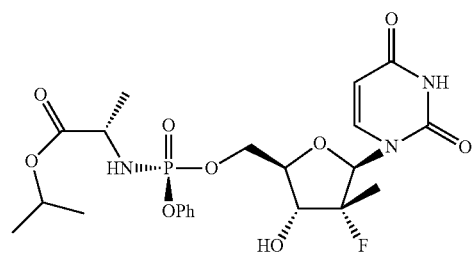
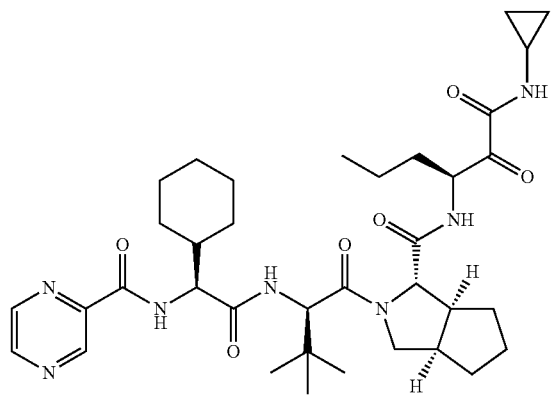
Telaprevir (VX-950)
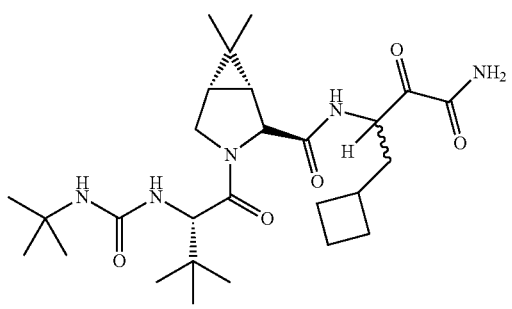
Boceprevir
-continued
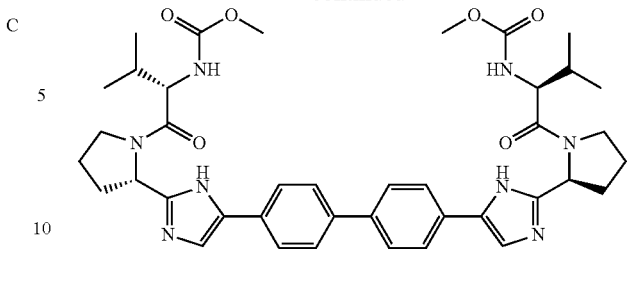
BMS-790052
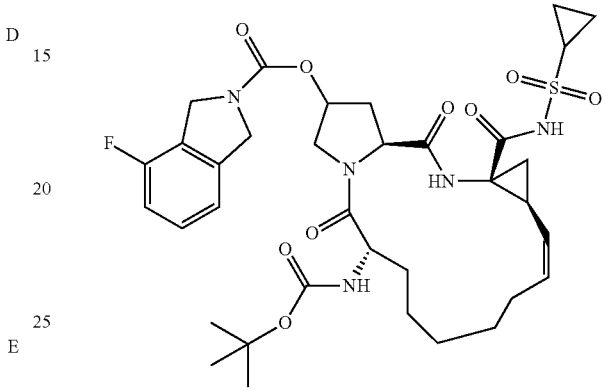
ITMN-191
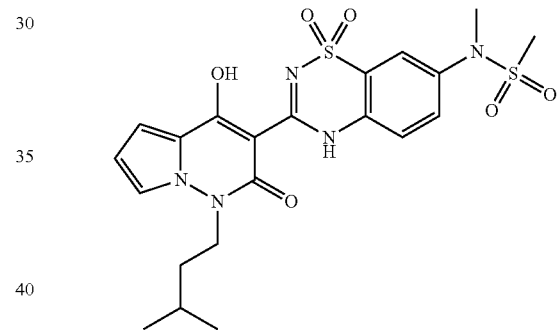
ANA-598
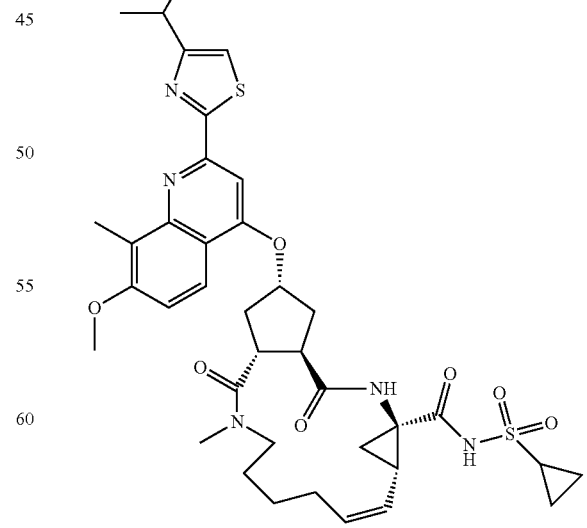
TMC435 as well as, interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor.

When crystalline or crystal-like 1.mH$_2$O or 1.nS are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

Preparation

A ninth embodiment is directed to process for preparing crystalline or crystal-like 1.mH$_2$O or 1.nS, which comprises crystallizing 1.mH$_2$O or 1.nS, wherein m and n are as defined above.

A first aspect of the ninth embodiment is directed to a process for preparing crystalline or crystal-like 1.mH$_2$O or 1.nS, further comprises dissolving or suspending 1 in a solvent or solvent mixture.

A second aspect of the ninth embodiment is directed to a process for preparing crystalline or crystal-like 1.mH$_2$O or 1.nS, which further comprises adding seed crystals of 1.mH$_2$O or 1.nS.

A third aspect of the ninth embodiment is directed to a process for preparing crystalline or crystal-like 1.mH$_2$O or 1.nS, which further comprises adding an anti-solvent to the solvent or solvent mixture.

Any suitable solvent may be used that affords crystalline or crystal-like 1.mH$_2$O or 1.nS. Specific solvents contemplated include, but are not limited to, anisole, ethyl acetate; xylenes; toluene; isopropanol; acetone; dichloromethane; diethyl ether; isopropyl acetate; t-Butyl methyl ether; or combinations thereof. Specific combinations include, but are not limited to, anisole/ethyl acetate; heptanes/ethyl acetate; xylenes/ethyl acetate/water; anisole/water; ethyl acetate/xylenes; isopropanol/xylenes; acetone/xylenes; dichloromethane/xylenes; dichloromethane/hexanes; ethyl acetate/toluene; diethyl ether/xylenes; isopropyl acetate/xylenes; isopropyl acetate/heptanes; ethyl acetate/water; t-butyl methyl ether/water; t-butyl methyl ether/ethyl ether; or t-butyl methyl ether. For solvent combinations that also include water, it is understood that a sufficient amount of water is required to form 1.mH$_2$O (when m≠0), which is based on an estimation of the amount of 1 used for the crystallization or the amount of 1 contained in a mixture containing 1 and its Rp-isomer. It is also understood that commercially available solvents contain a certain amount of water that might be sufficient, alone, to provide sufficient water for the formation of crystalline or crystal-like 1.mH$_2$O (when m≠0).

A tenth embodiment is directed to a method for determining the crystallinity of crystalline or crystal-like 1.mH$_2$O, which comprises analyzing 1.mH$_2$O by XRPD or single-crystal X-ray crystallography.

EXAMPLES

The following examples are intended to provide one of ordinary skill with a better understanding the disclosed embodiments.

Preparation of 1

Compound 1 may be prepared by stereoselective or non-stereoselective means. A stereoselective process is described below, as well as U.S. Provisional Patent Application No. 61/319,548, which is incorporated by reference. A non-stereoselective process is also described below, as well as in U.S. patent application Ser. No. 12/645,765, the subject matter of which is incorporated by reference. Production of 1 via the non-stereoselective process, which produces a diastereomeric mixture containing 1 and its Rp-isomer, further includes, as detailed below, crystallization of the diastereomeric mixture to obtain 1 or chromatographic separation of the diastereomeric mixture by way of SMB chromatography.

Example 1

Stereoselective Preparation of 1

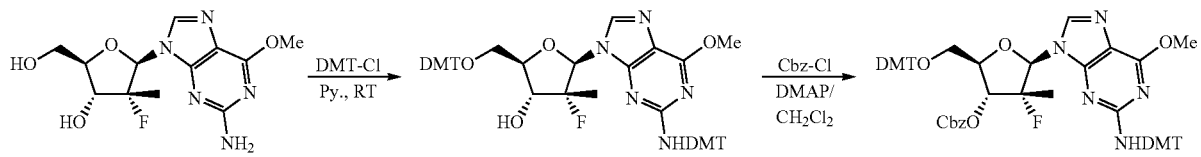

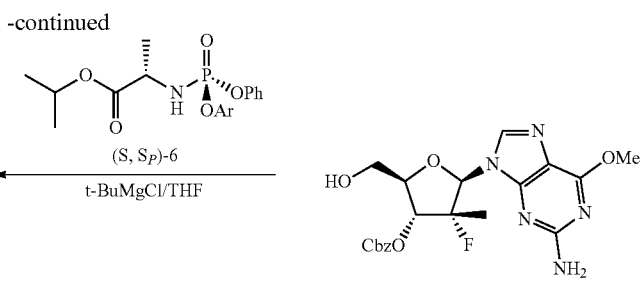
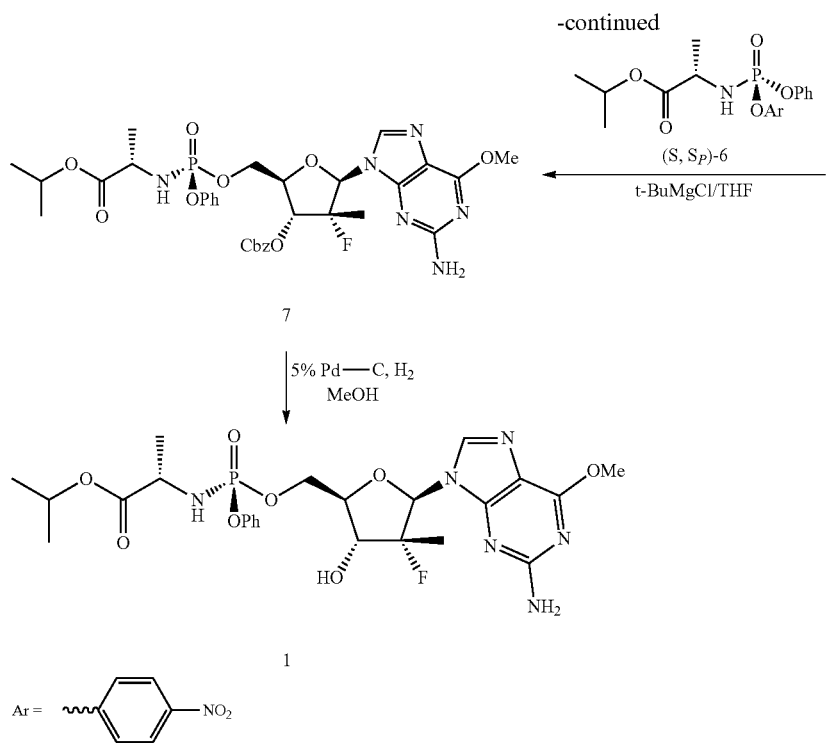

Example 1-1

Synthesis of (2R,3R,4R,5R)-2-((bis(4-methoxyphenyl)(phenyl)methoxy)methyl)-5-(2-((bis(4-methoxyphenyl)(phenyl)methyl)amino)-6-methoxy-9H-purin-9-yl)-4-fluoro-4-methyltetrahydrofuran-3-ol (3):

To a solution of (2R,3R,4R,5R)-5-(2-amino-6-methoxy-9H-purin-9-yl)-4-fluoro-2-(hydroxymethyl)-4-methyltetrahydrofuran-3-ol (2, 4 g, 12.8 mmol) in anhydrous pyridine (100 mL) cooled at 0° C. was added DMT-Cl portion-wise under nitrogen. The brown solution was stirred at ambient temperature for 24 hours. The mixture was concentrated under reduced pressure to remove most of solvent and sat. NaHCO$_3$ (20 mL) was added. The mixture was diluted with water (150 mL) and EtOAc (120 mL). The organic layer was separated and washed with water (5×120 mL), brine and dried over Na$_2$SO$_4$. After removal of solvent, the residue was purified via column chromatography (20% EA in hexanes to 80% EA in hexanes) to afford 11.6 g of product, 3, as a white foam solid (quantitative yield). $^1$H-NMR (DMSO-d$_6$): δ 7.94 (s, 1H), 7.39-7.37 (m, 3 H), 7.26-7.14 (m, 17H), 6.84-6.80 (m, 8H), 5.58 (s, 1H), 4.04 (br, 1H), 3.71-3.70 (m, 14H), 3.68 (m, 1H), 3.48 (br, 2H), 3.20 (d, 1H), 0.88 (br, 3H).

Example 1-2

Synthesis of benzyl ((2R,3R,4R,5R)-2-((bis(4-methoxyphenyl)(phenyl)methoxy)methyl)-5-(2-((bis(4-methoxyphenyl)(phenyl)methyl)amino)-6-methoxy-9H-purin-9-yl)-4-fluoro-4-methyltetrahydrofuran-3-yl) carbonate (4)

To a solution of nucleoside 3 (2.52 g, 2.75 mmol) in anhydrous DCM (8 mL) was added DMAP (1.01 g, 8.2 mmol) and the solution was cooled at 0° C. in an ice-water bath. Cbz-Cl (0.77 g, 4.2 mmol) was added via a syringe to the mixture and resulted in a cloudy reaction mixture. The mixture was stirred at room temperature for 24 hours and sat. NaHCO$_3$ (10 mL) was added. The mixture was partitioned in DCM and water. The organic layer was dried over Na$_2$SO$_4$ and concentrated to a white foam solid. The residue was purified via column chromatography (10~60% EtOAc in hexanes) to afford 2.74 g product, 4, as a white foam solid (yield, 95%). $^1$H-NMR (CDCl$_3$): δ 7.87 (s, 1H), 7.41-7.16 (m, 24H), 6.79-6.75 (m 8H), 6.28 (s, 1H), 5.65 (br, 1H), 5.15 (s, 2H), 4.28 (d, 1 H), 3.79-3.71 (m, 15H), 3.55-3.52 (m, 1H), 3.39-3.36 (m, 1H), 0.93 (br, 3H).

Example 1-3

Synthesis of (2R,3R,4R,5R)-5-(2-amino-6-methoxy-9H-purin-9-yl)-4-fluoro-2-(hydroxymethyl)-4-methyltetrahydrofuran-3-yl benzyl carbonate (5)

A 1 vol % of TFA solution in DCM (50 mL) was added to a flask loaded with 4 (2.69 g, 2.56 mmol). The mixture was stirred at room temperature for 2 h and it was complete. Sat. NaHCO$_3$ (20 mL) was added and the mixture was partitioned in water and DCM. The organic layer was concentrated and solid residue was purified by column chromatography (silica gel, 0~5% 2-PrOH in DCM) to afford 1.01 g of product, 5, as a white foam solid (yield 88%). $^1$H-NMR (CDCl$_3$): δ 7.82 (s, 1H), 7.39-7.33 (m, 5H), 6.02 (d, 1H, J=19.2 Hz), 5.77 (dd, 1H, J=20.8, 8.8 Hz), 5.32-5.30 (m, 1H), 5.20 (s, 2H), 5.04 (s, 2H), 4.34 (d, 1H, J=8.8 Hz), 4.15 (m, 1H), 4.04 (s, 3H), 3.85-3.79 (m, 1H), 1.21 (d, 3H, J=22.8 Hz).

Example 1-4

Preparation of (S)-2-[(4-nitro-phenoxy)-phenoxy-phosphorylamino]propionic acid isopropyl ester (Mixture of Diastereomers (S, S$_P$)-6 and (S, R$_P$)-6))

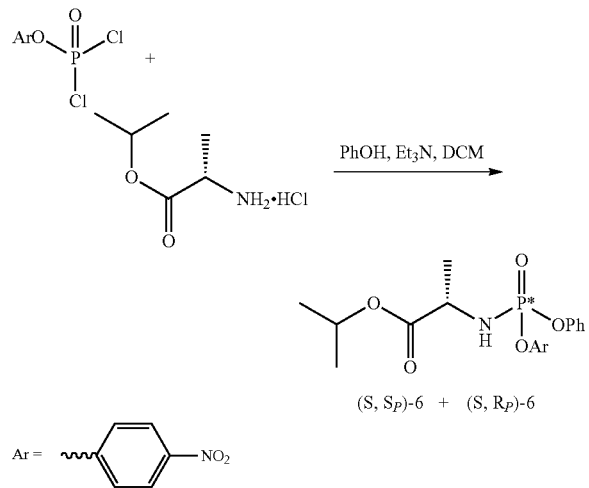

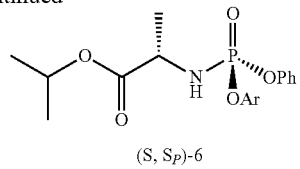

To a stirred solution of 4-nitrophenyl phoshorodichloridate 12.8 g, 50 mmol) in dichloromethane (100 mL) was added a solution of phenol and triethylamine (7.7 mL, 55 mmol) in dichloromethane (100 mL) at −78° C. over a period of 20 min. The mixture was stirred at this temperature for 30 min and then transferred to another round bottom flask containing L-alanine isopropyl ester hydrochloride (8.38 g, 50 mmol) in dichloromethane (100 mL) at 0° C. To the mixture was added second lot of triethylamine (14.6 mL, 105 mmol) over a period of 15 min. The mixture was stirred at 0° C. for 1 h and then the solvent was evaporated. The residue was triturated with ethyl acetate (150 mL) and the white solid was filtered off. The filtrate was concentrated under reduced pressure to give pale yellow oil. The crude compound was chromatographed using 0-20% ethyl acetate/hexanes gradient to give product (17 g, 83% yield) as a mixture of diastereomers in about 1:1 ratio. $^{31}$P NMR (162 MHz, CDCl$_3$): δ −2.05, −2.10; $^1$H NMR (400 MHz, CDCl$_3$): δ 8.22 (d, J=9.2 Hz, 2H), 7.41-7.33 (m, 4H), 7.26-7.18 (m, 3H), 5.05-4.96 (m, 1H), 4.14-4.05 (m, 1H), 3.93-3.88 (m, 1H), 1.38 (d, J=6.8 Hz, 3H), 1.22 (dd, J=6.2 & 3.0 Hz, 6H); MS (ESI) m/z 407 (M-1)$^+$.

Example 1-5

Crystallization of (S)-2-[(S)-(4-nitro-phenoxy)-phenoxy-phosphorylamino] propionic acid isopropyl ester ((S, S$_P$)-6

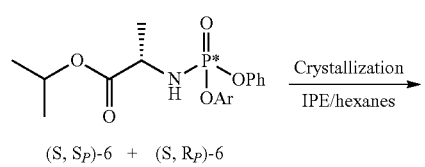

(S)-2-[(4-Nitro-phenoxy)-phenoxy-phosphorylamino]-propionic acid isopropyl ester (3.4 g) was dissolved in IPE (6 mL). To the above solution were added hexanes (1 mL) while hand shaking until the solution was turbid. Few drops of IPE were then added to the mixture to get a clear solution. The mixture was gently stirred at room temperature for 20 h. A white and fine crystalline solid obtained was filtered, washed with 1:1 mixture of IPE/hexanes and dried to give white fluffy solid (820 mg, 24% yield) mp 52 (shrinks) 62-66 (melts). $^{31}$P NMR (162 MHz, CDCl$_3$): δ −2.05; $^1$H NMR (400 MHz, CDCl$_3$): δ 8.22 (d, J=9.2 Hz, 2H), 7.41-7.33 (m, 4H), 7.26-7.18 (m, 3H), 5.05-4.96 (m, 1H), 4.14-4.05 (m, 1H), 3.93-3.88 (m, 1H), 1.38 (d, J=6.8 Hz, 3H), 1.22 (dd, J=6.2 & 3.0 Hz, 6H); MS (ESI) m/z 407 (M-1)$^+$. The stereochemistry of (S, S$_P$)-6 as having the CIP configuration of S has been confirmed by single crystal X-ray crystallography, see U.S. 61/319,548, filed on Mar. 31, 2010.

Example 1-6

Synthesis of S$_P$-(2S)-isopropyl 2-(((((2R,3R,4R,5R)-5-(2-amino-6-methoxy-9H-purin-9-yl)-3-(((benzyloxy)carbonyl)oxy)-4-fluoro-4-methyltetrahydrofuran-2-yl)methoxy)(phenoxy)phosphoryl)amino) propanoate (7)

To a solution of the nucleoside 5 (150 mg, 0.34 mmol) in 1.5 mL of anhydrous THF was added a solution of t-BuMgCl in THF (1.0 M, 0.41 mL) at 0° C. The cloudy mixture was stirred at ambient temperature for 1 h and then a solution of phosphoramidate reagent (ca 95% chiral purity) (S)-2-[(S)-(4-nitrophenoxy)phenoxyphosphorylamino]propionic acid isopropyl ester, (S, S$_P$)-6, (162 mg, 0.4 mmol) in 1.5 mL of THF was added to the mixture via a syringe drop-wise. (Compound 6 is prepared according to the procedures outlined in U.S. patent application Ser. No. 12/645,765.) The mixture was stirred at ambient temperature for 20 h and ca 29% of starting material remained. The reaction was quenched by adding sat. NH$_4$Cl (4 mL) and 20 ml, of EtOAc was added. After separation, organic layer was washed with water (3×25 mL), brine and dried over Na$_2$SO$_4$. After removal of solvent, the oil residue was checked by $^1$H-NMR and $^{31}$P-NMR. The ratio of two isomers was ca. 12.5:1. The major isomer, $^1$H-NMR (CDCl$_3$): δ 7.73 (s, 1H) (not completed); $^{31}$P-NMR (CDCl$_3$): δ 4.02.

Example 1-7

Synthesis of S$_P$-(2S)-isopropyl 2-(((((2R,3R,4R,5R)-5-(2-amino-6-methoxy-9H-purin-9-yl)-4-fluoro-3-hydroxy-4-methyltetrahydrofuran-2-yl)methoxy)(phenoxy)phosphoryl)amino)propanoate (1)

To a solution of crude phosphoramidate 7 in MeOH (2.5 mL) was added 5% Pd on charcoal (40 mg). The atmosphere in the flask was exchanged with hydrogen twice. The mixture was stirred at ambient temperature under one atmosphere of hydrogen for 1 h. The mixture was filtered through a short pad of Celite and the filtrate was concentrated. The crude residue was checked by $^1$H-NMR and $^{31}$P-NMR and ratio of two isomers was ca. 17:1 $S_P$ isomer (1) and also matched the $S_P$-isomer by thin layer chromatography. $^{31}$P-NMR (DMSO-$d_6$): δ 4.91.

Alternatively, 1 can be prepared directly from 2, as illustrated below.

Example 2

Synthesis of $S_P$-(2S)-isopropyl 2-(((((2R,3R,4R,5R)-5-(2-amino-6-methoxy-9H-purin-9-yl)-4-fluoro-3-hydroxy-4-methyltetrahydrofuran-2-yl)methoxy)(phenoxy)phosphoryl)amino)propanoate, 1

To a 50 mL of dry flask were added the nucleoside (2, 100 mg, 0.32 mmol) and 1.5 mL of anhydrous THF. The suspension was cooled in an ice bath and a solution of t-BuMgCl in THF (1.7 M, 0.35 mL, 2 eq) was added via a syringe slowly. The resulting clear solution was stirred at room temperature for one hour. A solution of chiral enriched phosphoramidate reagent (98:2 (S, $S_P$)-6/(S, $R_P$)-6, 156 mg, 0.383 mmol) in 1.5 mL of anhydrous THF was added via a syringe at room temperature dropwise. After 48 h, TLC indicated approximately 35% of the starting nucleoside remained. The reaction was quenched by adding sat. NH$_4$Cl (6 mL). Ethyl acetate (20 mL) was added and organic layer was separated. Aqueous layer was extracted with ethyl acetate (10 mL). Combined organic layer was washed with water (2×20 mL), sat NaHCO$_3$ (15 mL), water (3×25 mL), brine, and dried over Na$_2$SO4. After removal of solvent, the crude residue was checked by NMR. $^{31}$P NMR indicated a ratio of diastereomers was 75:1 (1/$R_P$-isomer of 1). The mixture was purified via column (silica gel, 0-8% MeOH in DCM) to afford product as a white foam solid (35.8 mg, 19%).

Non-Stereoselective Preparation of 1

Example 3

Synthesis of (2S)-isopropyl 2-((((2R,3R,4R,5R)-5-(2-amino-6-methoxy-9H-purin-9-yl)-4-fluoro-3-hydroxy-4-methyltetrahydrofuran-2-yl)methoxy)(phenoxy)phosphorylamino)propanoate (1)

To a 250 mL dry round-bottomed flask were loaded phenyl dichlorophosphate (2.66 g, 12.61 mmol) and anhydrous dichloromethane (40 mL). The amino ester salt (2.60 g, 15.53 mmol) was added to the solution and the mixture was cooled to −5° C. N-Methyl imidazole (7.7 mL, 97 mmol) was then added quickly via a dry syringe at −5° C. and the solution was stirred at −5° C. for 1 h. The nucleoside (1, 3.04 g, 9.7 mmol) was added from a vial in one portion at −5° C. and the solid was slowly dissolved in 20 minutes. The reaction temperature was allowed to rise to ambient temperature over 2 h. After 17 h, the reaction was not complete. More reagents were made (as described above from phosphate (2.66 g), aminoester (2.60 g), and NMI (3.8 mL, 48 mmol)) and added to the reaction mixture at −5° C. The reaction was stirred at room temperature for 2 more hours. The reaction was almost complete as shown by TLC result and diluted with 70 mL of dichloromethane. HCl solution (1 N, 70 mL) was added. The aqueous layer was separated and extracted with dichloromethane. The organic layer was washed with saturated NaHCO$_3$, water, brine and dried over MgSO$_4$. After removal of the solvent under reduced pressure, the sticky residue was purified through automated column chromatography using a 240 g cartridge and a gradient of 0-8% 2-PrOH in dichloromethane to afford product as a foam solid (4.16 g, 7.14 mmol, 73% yield). HPLC purity 97.4%. NMR spectra of product showed it is a mixture of two diastereoisomers with a ratio of 1.2:1.

$^1$H-NMR (DMSO-$d_6$): δ=7.98 (1H, s, 8-H of one isomer), 7.95 (1H, s, 8-H of another isomer), 7.37-7.32 (2H, m, arom-H), 7.22-7.15 (3H, m, arom-H), 6.6 (2H, s, NH$_2$), 6.11 (1H, d, C1'-H of one isomer), 6.09 (1H, d, C1'-H of another isomer), 6.09-5.98 (1H, m, amide NH), 5.88 (1H, d, 3'-OH of one isomer), 5.81 (1H, d, 3'-H of another isomer), 4.85-4.75 (1H, hepta, methine H of iso-propyl), 4.46-4.27 (2H, m, C4'-H, α-H of amino ester), 4.15-4.07 (1H, m, C3'-H), 3.96 (3H, s, OCH$_3$), 3.82-3.72 (2H, m, C5'-H$_a$ and C5'-H$_b$), 1.23-1.06 (9H, m, CH$_3$'s of amino ester), 1.03 (3H, d, C2'-CH$_3$).

$^{31}$P-NMR (DMSO-$d_6$): δ=4.91 (one isomer), 4.72 (another isomer).

An alternate purification method is to chemically alter the minor 3' phosphoramidate by-product in order to simplify the chromatographic separation. The crude phosphoramidate product is dissolved in anhydrous pyridine (5 mL/g), and is treated with 0.5 molar equivalents of t-butyldimethylsilyl chloride at ambient temperature to react selectively with the free 5' primary hydroxyl of the 3' isomer impurity. Reaction progress can be monitored by LC/MS. Once the 3' isomer is converted to a 5'-tBDMS-3'-phosphoramidate derivative, the reaction is quenched with methanol (3 eq), concentrated under reduced pressure, partitioned between ethyl acetate and 5% citric acid and then the organic layer is concentrated. The residue is then subjected to chromatography which can now be done with a higher loading and a faster gradient and achieve a higher purity.

Production of 1 via a non-stereoselective process provides for a diastereomeric mixture containing 1 and the Rp-isomer, whereby 1 can be further purified by crystallization of the mixture or by chromatographic separation, as illustrated below.

Example 4

Separation of 1 from a Mixture Containing 1 and the Rp-Isomer

Separate a total of 11.9 Kg of a diastereomeric mixture containing 1 and the Rp-isomer to obtain an approximate 85% yield of both isomers (1 and Rp-isomer) under cGMP protocols. The diastereomeric purity requirement is >98% d.e. for both diastereomers.

Preparative Chromatographic Conditions

The chromatographic equipment and separation method are as follows:

A 5-cm SMB system, consisting of 8 columns, each holding 100 grams of CHIRALPAK®IA™, was used for processing of the diastereomeric mixture. The mobile phase was 100% ethyl acetate.

Separation and Isolation

The solubility of this material was 75 g/l in the mobile phase. The material was dissolved in the mobile phase at 40° C. with stirring.

The extract stream from the SMB was first concentrated using a ½ sq ft horizontal thin-film evaporator (Protherm) and then dried down in the rotovap at 40° C. The flow rate of the raffinate stream was too low to be handled by the Protherm. The raffinate was directly dried down using the rotovap. The products were then dried to constant weight in a vacuum oven at 40° C. The residual level of ethyl acetate however was found to exceed the desired level (<0.4 wt %) even after constant weight had been reached. After further drying under vacuum at 50° C., the level remained at approximately 1 wt %. The products were re-dissolved in acetone and then evaporated to dryness in the rotovap. This step effectively removed the residual ethyl acetate level to below 0.1 wt %. The products were then further dried in the vacuum oven to reduce the residual acetone to the desired level of <0.4 wt %.

Results

Extract—1. A quantity of 6,864 g of amorphous 1 was recovered with a diastereomeric purity of 99.2% d.e.

Raffinate—The Rp-isomer. A quantity of 3,707 g of the Rp-isomer was recovered, of which 1,844 g had a diastereomeric purity of 98.1% d.e.

Example 5

Kiloscale Crystallization of 1.H$_2$O from Amorphous Solid 1 (Obtained from SMB Chromatography) with Anisole/Ethyl Acetate/Water A 10 L rotary evaporator flask was equipped with a mechanical stirrer. 1000 g of amorphous solid (98.9% HPLC purity, 0.25 molar equiv of water present) was added followed by ethyl acetate (1.00 L) and anisole (99% grade, 4.00 L) at ambient temperature. The suspension was rapidly stirred until all the solid dissolved (15 min). Stirring was slowed to 88 rpm. Crystalline seeds (40 mg) were added, followed by water (31 mL, 1.0 eq). The solution became cloudy after about 30 minutes and showed heavy precipitate after 3-4 h with no visible water remaining. The suspension was stirred for a total of 20 h at ambient temperature. The crystalline solid was collected by vacuum filtration on a 25 cm Buchner funnel. The cake washed with a 50:50 mixture of heptanes and t-butyl methyl ether (3×1 L). The cake washed easily and did not require pressing. After air-drying for 15 min, the solid was transferred to a 8×14" drying pan and dried under vacuum (0.2 mm Hg, 50° C.) to a constant weight (4 h) and then held under vacuum at ambient temperature for 17 h to yield 840 g (ca 82% for the difference in hydration) of fine broken crystalline laths and needles less than 150 micrometers on a side. HPLC purity 99.7%. The apparent melting point showed shrinking starting at 88° C. and melting at 93-100° C. As a hydrate, this represents a combination of dehydration to an amorphous solid and then the phase transition temperature.

The crystallization was repeated on 990 g more in a proportional manner to yield another 840 g (ca 83%) in the same purity. The filtrates were combined and stripped under reduced pressure to a yellow oil, crude wt 450 g which still contained roughly 150 g of anisole. To this was added ethyl acetate (350 mL), more anisole (850 mL), water (9 g) and seeds (20 mg). The solution was stirred as before. It became cloudy after 4 h and stirred at ambient temperature for 24 h. The solid was collected by filtration and rinsed with 50:50 heptanes and t-butyl methyl ether while mechanically breaking up lumps and washing until a yellow tinge was gone (4×450 mL). The solid was dried in a similar manner to give 200 g more product in 98.9% HPLC purity which is suitable for an additional recrystallization. The mother liquor was stripped to 175 g of light brown oil (85% HPLC purity) still containing some anisole.

Example 6

Crystallization of 1.H$_2$O from Amorphous 1 (Obtained from SMB Chromatography) with Heptanes/Ethyl Acetate 1 g of the amorphous 1 (98.9% HPLC purity) was dissolved in mixture of ethyl acetate (4 mL) and heptanes (2 mL) by shaking on a Vortex mixer. To this solution was added a few seeds of crystalline product. The suspension was stirred at ambient temperature in an open vessel exposed to atmospheric moisture for 6 h. The solid was collected by filtration and washed with a mixture of ethyl ether and hexanes (1:1, 3×3 mL) and dried to 910 mg of crystalline solid. HPLC purity 99.5%.

Example 7

Crystallization of 1.H$_2$O from Amorphous 1 (Obtained from SMB Chromatography) with Xylenes/Ethyl Acetate/Water 1 g of the amorphous 1 (98.9% HPLC purity) was dissolved ethyl acetate (1.5 mL) and then xylenes was added until cloudy (3.2 mL). The mixture was heated to 45° C. to give a clear solution and then cooled to ambient temperature. Water (50 µL) was added and the solution was stirrer with a magnetic stirrer. No seeds were added. After 72 h, the resulting precipitate was collected by filtration, washed with 35% ethyl acetate in xylenes (2.5 mL) and dried (0.2 mm Hg, ambient temperature) to give 950 mg of product as fine white crushed crystals. HPLC purity 99.5%.

Discussion on Purification from Mixture.

A practical alternative to separating out 1 from a mixture containing 1 and its corresponding Rp-diastereomeric counterpart, by SMB chromatography and then crystallizing it is to crystallize 1 (or 1.H$_2$O) directly from the mixture. The overall recovery is nearly as high while avoiding the expense and time consumption of the SMB process. Direct crystallization of material produced with a chiral synthesis with a greatly enhanced $S_P/R_P$ ratio is expected to be even more efficient.

Example 8

Crystallization of 1.H$_2$O from Purified Amorphous Solid of Mixture of Isomers ($S_P/R_P$ (1.6:1))

A mixture containing 1 and its diastereomeric counterpart (the Rp isomer) (1.0 g) was dissolved in ethyl acetate (1 mL). Anisole (4 mL) was added slowly to form a clear solution with rapid stirring. Water (22 mg, 1.0 eq based on 1) was added followed by crystalline 1 seeds (~2 mg). The solid started to form in 10 min. Stirring was continued for 36 h. White solid was collected by filtration and washed with cold mixture of ethyl ether/hexanes (1:1, 3 ml×3). Yield=520 mg (96% 1 by P-NMR). 470 mg of this material was recrystallized by dissolving in warm ethyl acetate (0.7 mL, 45° C.) over 2 min, then with stirring, adding anisole (2.8 mL) with no additional water or seeds. The solution became cloudy after 5 min. It was stirred for 48 h at ambient temperature. The solid was collected by filtration in a sintered glass funnel, and washed with a cold mixture of ethyl ether/hexanes (1:1, 2 ml×3) and dried under vacuum to a white solid, 451 mg (>99% pure by P-NMR). Recovery percentage based on the 615 mg of 1 theoretically present in the starting mixture was 73%.

Discussion on Alternative Solvent Mixtures to Crystallize the $S_P$-Isomer from the Mixture.

A mixture containing 1 and the Rp-isomer (1 g) dissolved in ethyl acetate (4 mL/g) with a molar equivalent of water followed by evaporation to ca 1 mL/g yielded 396 mg of 93% pure material. A 375 mg sample of this was recrystallized form ethyl acetate (2.5 mL) and an equivalent of water to yield 275 mg of 99.1% pure material. Another 1 g of the diastereomeric mixture was crystallized from ethyl acetate/heptanes 2:1 (6.5 mL/g) with one equivalent of water to give 433 mg of 95% purity.

It is contemplated that $1.H_2O$ can be obtained by crystallization of crude mixtures of 1 and the $R_P$-isomer.

Alternatively, the $S_P$-isomer can also be isolated without any chromatography through direct crystallization of the monohydrate from the crude product formed from the chlorophosphate reagent (see non-stereoselective process above). Anisole-water is a suitable solvent combination to initiate the crystallization followed by dilution with ethyl ether. Other solvent combinations such as used on the purified 1 could also be used.

Example 9

Isolation of 1 by Crystallization Directly from the Crude Product

To a 50 mL dry round-bottomed flask were loaded phenyl dichlorophosphate (2.68 g, 12.7 mmol) and anhydrous dichloromethane (40 mL). The amino ester salt (2.58 g, 15.4 mmol) was added to the solution and the mixture was cooled to −30° C. N-Methyl imidazole (6.3 g, 76 mmol) was then added quickly via a dry syringe at −30° C. and the solution was stirred at −5° C. for 20 min. The nucleoside (7, 2.00 g, 6.38 mmol) was added from a vial in one portion at −5° C. and the solid was slowly dissolved in 20 minutes. The reaction temperature was allowed to rise to ambient temperature and stirred for 1 h. TLC indicated approximately 95% completion. The reaction was diluted dichloromethane (50 mL) and washed with 1 N HCl (2×50 mL), 1:1 mixture of sat'd bicarbonate and brine, dried over sodium sulfate (5 g), filtered, concentrated under reduced pressure and then high vacuum to 4.5 g of crude product. P-NMR indicated a 1.5:1 mixture of the $S_P/R_P$ isomers.

A small portion (100 mg) of the crude oil was dissolved in anisole (0.30 mL) and the solution was filtered through a syringe filter (22 micron). Water (8 mg) was added slowly to the stirred solution at ambient temperature followed by seed crystals (ca 1 mg). The solution became cloudy in 5 min. Ethyl ether (1 mL) was dropped in slowly and the suspension was stirred for 2 h and then the precipitate was collected by filtration, washed with a cold 1:1 mixture of ether ether-hexane (3×1 mL) and then dried under vacuum at ambient temperature to 17 mg of the Sp-isomer. NMR purity 98%. This represents a yield of 21% from the starting nucleoside and 35% of the theoretical yield of the amount of 1 formed in the crude mixture.

Discussion of Solid State Characterization.

Single crystal x-ray from methylene chloride/hexanes/atmospheric water indicated a single water molecule incorporated into the crystal structure. Samples from three solvent systems (anisole/ethyl acetate, heptanes/ethyl acetate, xylenes/ethyl acetate) all showed the same crystalline form by XRPD. The anisole sample was used for additional studies. Karl Fisher analysis showed 3.1% water which corresponds to a monohydrate. TGA analysis indicated a loss of a half hydrate between 80-100° C. and the second half hydrate at 110 to 170° C. DSC under heating at 10° C./min in an open pan indicated an endotherm starting at 75° C. for the dehydration with an onset of 93.56° C. and peak at 100.24° C. Variable temperature XRPD showed a loss of crystallinity between 90 and 100° C. GVS analysis showed very low hygroscopicity of the monohydrate with a reversible 0.47% w/w gain at 90% RH and stability of the monohydrate at 0% RH.

Example 10

XRPD of $1.H_2O$ (Form 1)

Experiment

X-Ray Powder Diffraction patterns were collected on a Bruker D8 diffractometer using Cu Kα radiation (40 kV, 40 mA), 0-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v 11.0.0.2 or v 13.0.0.2.

Samples were run under ambient conditions as flat plate specimens using powder as received. Approximately 20 mg of the sample was gently packed into a cavity cut into polished, zero-background (510) silicon wafer. The sample was rotated in its own plane during analysis. The details of the data collection are:

Angular range: 2 to 42 °2θ
Step size: 0.05 °2θ
Collection time: 0.5 s.step$^{-1}$ An XRPD pattern was obtained providing the following °2θ/% intensity data:

TABLE 1

XRPD data of $1 \cdot H_2O$.

| Angle 2-Theta ° | Intensity % | Angle 2-Theta ° | Intensity % |
|---|---|---|---|
| 8.0 | 9.6 | 23.4 | 18.8 |
| 8.7 | 48.2 | 24.4 | 9.1 |
| 9.1 | 12.2 | 24.7 | 21.0 |
| 10.3 | 6.0 | 25.2 | 10.8 |
| 11.1 | 30.5 | 25.5 | 7.1 |
| 11.3 | 11.6 | 25.9 | 20.6 |
| 11.8 | 7.7 | 26.5 | 5.5 |
| 13.6 | 34.9 | 27.0 | 9.9 |
| 14.1 | 19.2 | 27.1 | 13.7 |
| 14.8 | 100.0 | 27.4 | 23.8 |
| 15.3 | 6.4 | 28.1 | 8.6 |
| 15.6 | 5.1 | 28.5 | 11.5 |
| 16.1 | 18.2 | 28.9 | 5.1 |
| 16.8 | 24.2 | 29.8 | 6.9 |
| 17.6 | 99.8 | 30.1 | 7.7 |
| 17.8 | 37.5 | 30.5 | 7.4 |
| 18.8 | 4.7 | 31.7 | 7.4 |
| 19.4 | 8.3 | 32.7 | 5.0 |
| 20.4 | 64.0 | 33.4 | 5.4 |
| 21.7 | 8.5 | 33.9 | 4.1 |
| 22.1 | 23.2 | 35.0 | 5.0 |
| 23.0 | 12.0 | 36.1 | 5.5 |

FIG. 1 contains an XRPD spectrum of $1.H_2O$.

Example 11

X-ray Structure Determination of $1.H_2O$

Compound $1.H_2O$, $C_{24}H_{34}N_6PO_9F$, crystallizes in the orthorhombic space group $P2_12_12_1$ (systematic absences h00: h=odd, 0k0: k=odd, and 00l: l=odd) with a=10.9918(8)Å, b=13.0925(9)Å, c=20.3570(13)Å, V=2929.6(3)Å$^3$, Z=4, and $d_{calc}$=1.362 g/cm$^3$. X-ray intensity data were collected on a Bruker APEXII CCD area detector employing graphite-monochromated Mo-Kα radiation (k=0.71073 Å) at a temperature of 143(1)K. Preliminary indexing was performed from a series of thirty-six 0.5° rotation frames with exposures of 30 seconds. A total of 1790 frames were collected with a crystal to detector distance of 37.522 mm, rotation widths of 0.5° and exposures of 30 seconds:

| scan type | 2θ | ω | φ | χ | frames |
|---|---|---|---|---|---|
| φ | -15.50 | 258.48 | -351.72 | 19.46 | 739 |
| ω | -5.50 | 2.88 | -8.86 | -31.86 | 116 |
| φ | -10.50 | 300.13 | 18.75 | 39.97 | 196 |
| φ | 19.50 | 59.55 | -11.29 | -16.16 | 739 |

Rotation frames were integrated using SAINT (Bruker (2009) SAINT. Bruker AXS Inc., Madison, Wis., USA.), producing a listing of unaveraged $F^2$ and $\sigma(F^2)$ values which were then passed to the SHELXTL (Bruker (2009) SHELXTL. Bruker AXS Inc., Madison, Wis., USA.) program package for further processing and structure solution on a Dell Pentium 4 computer. A total of 47654 reflections were measured over the ranges 1.85≤θ≤25.06°, -13≤h≤13, -15≤k≤15, -24≤l≤22 yielding 5187 unique reflections (Rint=0.0261). The intensity data were corrected for Lorentz and polarization effects and for absorption using SADABS ((Sheldrick, G. M. (2007) SADABS. University of Gottingen, Germany.) (minimum and maximum transmission 0.6749, 0.7452).

The structure was solved by direct methods (SHELXS-97 (Sheldrick, G. M. (2008) Acta Cryst. A64, 112-122)). Refinement was by full-matrix least squares based on $F^2$ using SHELXL-97 (Sheldrick, G. M. (2008) Acta Cryst. A64, 112-122.) All reflections were used during refinement. The weighting scheme used was $w=1/[\sigma^2(F_o^2)+(0.0413P)^2+0.4916P]$ where $P=(F_o^2+2F_c^2)/3$. Non-hydrogen atoms were refined anisotropically and hydrogen atoms were refined using a riding model. Refinement converged to R1=0.0244 and wR2=0.0657 for 5000 observed reflections for which F>4σ(F) and R1=0.0259 and wR2=0.0669 and GOF=1.059 for all 5187 unique, non-zero reflections and 377 variables (R1=Σ||Fo|-|Fc||/Σ|Fo|; wR2=[Σw(Fo2-Fc2)2/Σw(Fo2)2]$^{1/2}$; GOF=[Σw(Fo2-Fc2)2/(n-p)]$^{1/2}$; where n=the number of reflections and p=the number of parameters refined.) The maximum Δ/σ in the final cycle of least squares was 0.001 and the two most prominent peaks in the final difference Fourier were +0.170 and -0.248 e/Å$^3$.

Table 2 lists cell information, data collection parameters, and refinement data. Final positional and parameters are given in Table 3. FIG. 2 is an ORTEP ("ORTEP-II: A Fortran Thermal Ellipsoid Plot Program for Crystal Structure Illustrations." C. K. Johnson (1976) ORNL-5138) representation of the 1·H$_2$O with 30% probability thermal ellipsoids displayed.
ellipsoids.

TABLE 2

| Summary of Structure Determination of 1·H$_2$O | |
|---|---|
| Empirical formula | C$_{24}$H$_{34}$N$_6$PO$_9$F |
| Formula weight | 600.54 |
| Temperature | 143(1) K |
| Wavelength | 0.71073 Å |
| Crystal system | orthorhombic |
| Space group | P2$_1$2$_1$2$_1$ |
| Cell constants: | |
| a | 10.9918(8) Å |
| b | 13.0925(9) Å |
| c | 20.3570(13) Å |

TABLE 2-continued

| Summary of Structure Determination of 1·H$_2$O | |
|---|---|
| Volume | 2929.6(3) Å$^3$ |
| Z | 4 |
| Density (calculated) | 1.362 Mg/m$^3$ |
| Absorption coefficient | 0.160 mm$^{-1}$ |
| F(000) | 1264 |
| Crystal size | 0.22 × 0.18 × 0.10 mm$^3$ |
| Theta range for data collection | 1.85 to 25.06° |
| Index ranges | -13 ≤ h ≤ 13, |
|  | -15 ≤ k ≤ 15, |
|  | -24 ≤ l ≤ 22 |
| Reflections collected | 47654 |
| Independent reflections | 5187 [R(int) = 0.0261] |
| Completeness to theta = 25.06° | 99.8% |
| Absorption correction | Semi-empirical from equivalents |
| Max. and min. transmission | 0.7452 and 0.6749 |
| Refinement method | Full-matrix least-squares on F$^2$ |
| Data/restraints/parameters | 5187/0/377 |
| Goodness-of-fit on F$^2$ | 1.059 |
| Final R indices [I > 2sigma(I)] | R1 = 0.0244, wR2 = 0.0657 |
| R indices (all data) | R1 = 0.0259, wR2 = 0.0669 |
| Absolute structure parameter | 0.03(6) |
| Largest diff. peak and hole | 0.170 and -0.248 e.Å$^{-3}$ |

The following embodiments provide examples where various phosphoramidate reagents are used to prepare 1, its R$_P$-isomer, or a diastereomeric mixture of 1 and its R$_P$-isomer.

Example 12-1

Synthesis of (S)-2-{(S)-[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester monohydrate (1) via (S)-isopropyl 2-(((S)-(perfluorophenoxy)(phenoxy)phosphoryl)amino)propanoate ((S, S$_P$)-8) and isolation by chromatography and crystallization

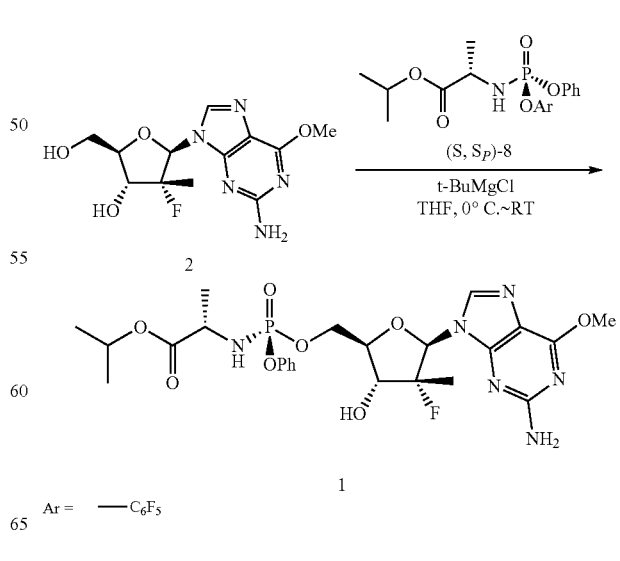

a) Preparation of (S)-2-[(2,3,4,5,6-pentafluoro-phenoxy)-phenoxy-phosphorylamino] propionic acid isopropyl ester ((S, S$_P$)-8 and (S, R$_P$)-8) and isolation of (S)-2-[(S)-(2,3,4,5,6-pentafluoro-phenoxy)-phenoxy-phosphorylamino] propionic acid isopropyl ester ((S, S$_P$)-8) via crystallization-induced dynamic resolution in a single crop To a 1 L of dry three-necked flask fitted with a low-temperature thermometer and a mechanical stirrer was loaded phenyl phosphorodichloridate (25 g, 118.5 mmol). Anhydrous dichloromethane (125 mL) was added and the solution was cooled to 0° C. The alanine ester salt (oven dried) (19.86 g, 1 eq) was added quickly under N$_2$ while agitated. The solution was cooled to ca –50° C. (internal temperature (in an acetone/dry ice bath under N$_2$). A solution of triethylamine (25.2 g, 2.1 eq) in DCM (125 mL) was added dropwise via an addition funnel over 0.5 h at –50° C. and the resulting white slurry was stirred at about –50° C. for 0.5 h. The mixture was allowed to warm up to 0° C. over 1.5 h and then a pre-mixed cooled solution of pentafluorophenol (21.82 g, 1 eq) and TEA (13.2 g, 1.1 eq) (caution: heat released while mixing pentafluorophenol and TEA) in 75 mL of DCM was added over 0.5 h at 0° C. via an addition funnel. The mixture was stirred at 0° C. for additional 4 h.

The mixture was filtered through a Buchner funnel and the collected solid triethylamine hydrochloride was rinsed with DCM (3×40 mL). The filtrate was checked by $^{31}$P-NMR (ratio ca 1.14:1 favored the S$_P$-diastereomer—downfield peak) and was divided into two parts of equal weight. One of them was concentrated under reduced pressure. The white solid residue (31 g) was triturated in a mixture of EtOAc and hexanes (150 mL, 20:80, v/v) at RT for 17 h allowing time for dynamic resolution of the less soluble S$_P$-isomer. The white slurry was filtered and solid was rinsed with 20% EtOAc in hexanes (2×25 mL). The solid (22.58 g) was checked by $^1$H-NMR and $^{31}$P-NMR and it contained product as one isomer contaminated with triethylamine hydrochloride salt. The solid was dissolved and partitioned in 310 mL of EtOAc and 100 mL of water. After separation of the organic layer, the aqueous layer was back-extracted with EtOAc (50 mL). The combined organic layer was washed with water (3×80 mL), brine (50 mL) and dried over MgSO$_4$. The solution was concentrated under reduced pressure and then dried under high vacuum at RT to a constant weight to furnish 17.36 g of product as a white solid from the one half of the reaction. The yield is 64%. The mother liquor from above was concentrated to a gummy residue (7.89 g) that contained the reagents with a ratio of 1:1.2 ((S, S$_P$)-8/(S, R$_P$)-8) based on $^{31}$P-NMR.

b) Preparation of 1 from (S, S$_P$)-8 and 2

To a 250 mL of dry three-necked round flask was added 5.06 g (16.15 mmol) of the purine nucleoside (2). The solid was suspended in 40 mL of anhydrous THF and cooled in an ice-water bath. The Grignard reagent (1 M solution in THF) was added dropwise via a syringe and a clear solution was formed. The mixture was stirred at 0° C. for 30 minutes and a solution of (S, S$_P$)-8 (8.32 g, 18.35 mmol) in 40 mL of THF was added via an addition funnel over 50 minutes. After finishing addition, the reaction mixture was stirred at room temperature for 3 hours. The reaction was quenched by adding 20 mL of sat NH$_4$Cl at 0° C. The mixture was diluted with 100 mL of ethyl acetate. Two layers were separated and aqueous layer was extracted with 50 mL of ethyl acetate. Organic layer was combined and washed with water (60 mL), sat sodium bicarbonate (2×60 mL), water (60 mL), brine (40 mL), and dried over sodium sulfate. Solvent was removed under reduced pressure to afford an amorphous solid residue.

To the crude residue 7 mL of ethyl acetate was added and followed by 26 mL of anisole. The mixture was stirred until a solution was formed. Water (320 mg) was added and 20 mg of crystal seeds of product (1) was added. The mixture was cooled at –5° C. overnight. White solid was formed and collected by filtration. Solid was rinsed with pre-cooled mixture of heptane and TBME (1:1, 3×2 mL) and weighed 3.3 g after drying. The mother liquor was concentrated under reduced pressure and the residue was purified via column chromatography (5~7% 2-propanol in DCM). Product was obtained as a white amorphous solid (4.5 g).

Solids from above were combined (7.8 g) and mixed with 7.7 mL of ethyl acetate. To the slurry, 31 mL of anisole was added and the mixture was stirred until a uniform solution was formed. To the solution 160 mg of water was added and followed by 20 mg of crystal seeds of product (1). The mixture was stirred slowly at room temperature and white solid precipitated. The mixture was kept at –5° C. for 2 hours and solid was collected via filtration. Solid was rinsed with pre-cooled mixture of heptane and TBME (1:1, 4×5 mL) and dried in vacuo. Product weighed 6.69 g (69% yield).

Example 12-2

Synthesis of (S)-2-{(S)-[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester monohydrate (1) via (S)-isopropyl 2-(((S)-(perfluorophenoxy)(phenoxy)phosphoryl)amino)propanoate ((S, S$_P$)-8) and isolation by crystallization only To a 250 mL of dry three-necked round flask were loaded 5 g (15.96 mmol) of the nucleoside and 40 mL of anhydrous THF. The suspension was cooled in an ice-water bath and 20 mL of the Grignard reagent (1 M solution in THF, 20 mmol) was added via a syringe over 10 minutes. The clear reaction mixture was stirred at 0° C. for half hour and then a solution of the phosphorus reagent ((S, S$_P$)-8) in 40 mL of THF was added via an addition funnel in 2 hours. The reaction was allowed to warm up to ambient temperature slowly and stirred for overnight. The mixture was cooled to 0° C. and 50 mL of 1 N diluted HCl was added. Most of THF was removed under reduced pressure and the mixture was diluted with 200 mL of ethyl acetate. The organic layer was separated and aqueous layer was extracted with 30 mL of ethyl acetate. The combined organic layer was washed with water (60 mL), sat'd. sodium bicarbonate (2×50 mL), 5% sodium carbonate (70 mL), water (50 mL), and brine (50 mL). Organic solution was dried over magnesium sulfate and solvent was removed under reduced pressure to afford an amorphous solid residue.

The crude residue was dissolved in 41 mL of anisole at room temperature. To the solution, 24 mL of xylenes was added and followed by 410 mg of water. The mixture was stirred slowly at room temperature and crystal seeds of 1 (10 mg) were added. White solid precipitated and the mixture was kept at –5° C. for 2 hours. Solid was collected via filtration and rinsed with a pre-cooled mixture of heptane and TBME (1:1, 3×2 mL). Solid weighed 5.83 g after drying. The mother liquor was concentrated to dryness under reduced pressure. The residue was dissolved in 7.2 mL of anisole and 10.7 mL of xylenes was added. To the solution, 178 mg of water was added and 5 mg of crystal seeds of 1 were added. The mixture was slowly stirred at room temperature for overnight. White solid was formed and collected via filtration. Solid was rinsed with a pre-cooled mixture of heptane and TBME (1:1.3×1 mL) and weighed 1.17 g.

Solids obtained above were combined (7.0 g) and added 7 mL of ethyl acetate. After addition of 27 mL of anisole, a clear solution was formed. To the solution, 200 mg of water was added and then added 5 mg of crystal seeds of 1. The mixture was stirred at ambient temperature and white solid precipitated. The mixture was kept at −5° C. for overnight. Crystalline solid was collected by filtration and rinsed with a pre-cooled mixture of heptane and TBME (1:1, 3×5 mL). The resultant product (1) weighed 5.66 g with purity of 98.3% by HPLC.

The above solid was purified again via crystallization from a combination of 5.6 mL ethyl acetate and 22.6 mL of anisole. After filtration and drying, 4.48 g (47%) of product was obtained and purity was 99.18% by HPLC. Spectral ($^1$H- and $^{31}$P-NMR, MS) and physical properties (HPLC retention, melting point and appearance) matched an authentic sample.

Example 12-3

Synthesis of (S)-2-{(S)-[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester (1) via (S)-isopropyl 2-(((S)-(2,4-dinitrophenoxy)(phenoxy)phosphoryl)amino)propanoate ((S, S$_P$)-9)

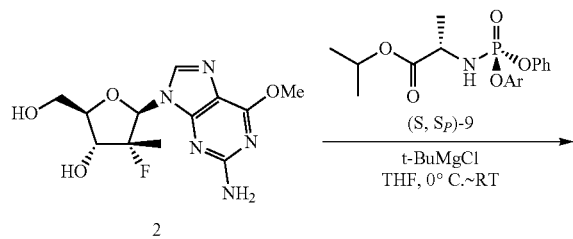

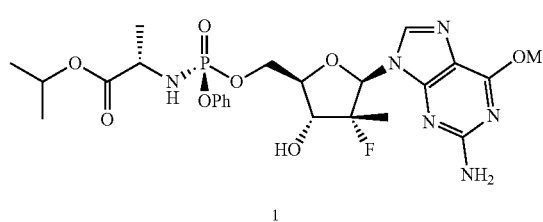

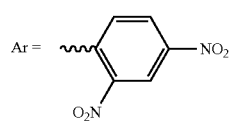

a) Preparation of (2S)-isopropyl 2-(((2,4-dinitrophenoxy)(phenoxy)phosphoryl)amino)propanoate diastereomeric mixture ((S, S$_P$)-9 and (S, R$_P$)-9) and isolation of the single isomer (2S)-isopropyl 2-(((S)-(2,4-dinitrophenoxy)(phenoxy)phosphoryl)amino)propanoate ((S, S$_P$)-9) by crystallization

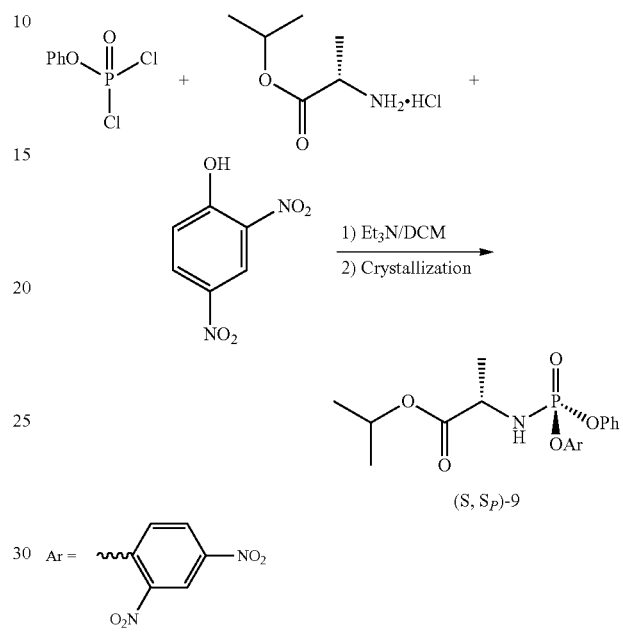

Phenyl phosphorodichloridate (10.0 g, 47.4 mmol) was dissolved in 60 mL of dry DCM and subsequently cooled to −78° C. A premixed solution of 2,4-dinitrophenol (8.72 g, 47.4 mmol) and triethylamine (7.27 mL, 52.1 mmol) in 20 mL of DCM was slowly added at −78° C. over a period of 30 min. The reaction was brought to 0° C. and stirred for 2.5 h at this temperature before (L)-alanine isopropyl ester (7.95 g, 47.4 mmol) was added as a solid in one batch. Stirring for 40 min at 0° C. was then followed by addition of more triethylamine (13.9 mL, 99.54 mmol) and additional stirring for 3 h at 0° C. or until judged complete by TLC (ethyl acetate/hexane=1/3). The reaction mixture was subsequently evaporated under reduced pressure, residue redissolved in MTBE (100 mL), solids filtered off and filtrate evaporated to dryness to give yellow syrup. NMR of the crude sample indicated mixture of 2 isomers ((S, S$_P$)-9 and (S, R$_P$)-9) in the ratio of 1:1. A mixture of EtOAc:Hexanes (1:1) (50 ml) was added and mixture allowed to stir for 15 h. The white solid thus formed was filtered off and rinsed with EtOAc:Hexanes (1:1) (20 mL) and dried under vacuum to give 6.0 g (28%) of (S, S$_P$)-9 a single isomer.

Data: $^1$H NMR (CDCl$_3$, 400 MHz) δ: 8.82-8.81 (m, 1H), 8.43-8.40 (m, 1H), 7.89-7.86 (m, 1H), 7.36-7.32 (m, 2H), 7.23-7.19 (m, 3H), 4.96 (hepta, 1H), 4.19-4.08 (m, 2H), 1.42 (d, 3H), 1.20 (d, 6H). $^{31}$P NMR (CDCl$_3$, 162 MHz) δ: −1.82.

b) Preparation of 1 from (S, S$_P$)-9 and 2

To a 50 mL of dry round-bottomed flask were added 80 mg (0.255 mmol) of 2 and 1 mL of anhydrous THF. The suspension was cooled in an ice water bath and 0.33 mL of Grignard reagent was added via a syringe under nitrogen. A clear solution was formed and stirred at 0° C. for half hour. A solution of (S, $S_P$)-9 (133 mg, 0.294 mmol) in 1.5 mL of THF was added via a syringe. The orange-colored, clear, reaction mixture was checked by TLC in 20 minutes at 0° C. and the reaction was almost complete. Product was formed as well as the 3',5'-bisphosphoramidate by-product. The reaction was quenched by adding sat NH$_4$Cl after one and half hour. The mixture was diluted with 20 mL of ethyl acetate. Organic layer was separated and aqueous layer was extracted with ethyl acetate (20 mL). The combined organic layer was washed with water (50 mL), sat sodium bicarbonate (2×40 mL), sat sodium carbonate (40 mL), water (40 mL), and brine (30 mL). The light yellow color organic layer was dried over sodium sulfate. The solution was concentrated under reduced pressure and an amorphous solid residue resulted was purified via column chromatography. The bis-phosphoramidate by-product was eluted out at 1% methanol in DCM as a foam solid (32.4 mg) and 1 was eluted out at 3% methanol in DCM (74 mg, 0.127 mmol, 49.6%).

Example 12-4

Synthesis of (S)-2-{[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester diastereomeric mixture (1 and Rβ isomer) via (2S)-isopropyl 2-(((2-nitrophenoxy)(phenoxy)phosphoryl)amino)propanoate (((S, $S_P$)-10 and (S, $R_P$)-10)

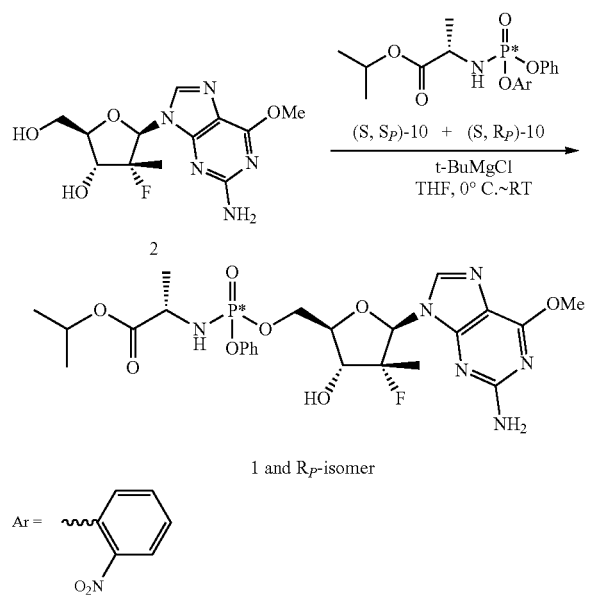

a) Preparation of ((S, $S_P$)-10 and (S, $R_P$)-10)

To a solution of phenyl phosphorodichloridate (30 g, 142.2 mmol) in dichloromethane (150 mL) at −70° C. under nitrogen atmosphere was added drop wise a pre-prepared mixture of o-Nitro phenol (19.76 g, 142.2 mmol) and triethylamine (19.8 mL, 142.2 mmol) in dichloromethane (150 mL) through addition funnel for 1 h at above temperature. Stirring was continued for additional 2 h and was slowly brought to 0° C. L-alanine isopropyl ester hydrochloride salt (26.2 g, 156.3 mmol) was added as solid and then followed by triethylamine (43.7 mL, 313.4 mmol) in dichloromethane (150 mL) drop wise at 0° C. for 20 min. and the reaction mass was continued stirring at the same temperature for additional one hour. The reaction mixture was filtered and concentrated and was finally purified by column chromatography (20% EtOAc/hexanes) on a silica gel to yield ((S, $S_P$)-10 and (S, $R_P$)-10) as diastereomeric mixture (14.4 g, 25%). $^1$H NMR (CDCl$_3$, 400 MHz) δ: 7.94-7.90 (m, 1H), 7.67-7.63 (m, 1H), 7.57-7.54 (m, 1H), 7.33-7.26 (m, 3H), 7.23-7.14 (m, 3H), 5.04-4.89 (m, 1H), 4.21-4.04 (m, 2H), 1.38 (d, 3H, isomer I), 1.33 (d, 3H, isomer II), 1.23-1.17 (m, 6H). $^{31}$P NMR (CDCl$_3$, 162 MHz) δ: −1.55 (isomer I), −1.76 (isomer II).

b) Preparation of Diastereomeric Mixture of 1 and its $R_P$-Isomer from ((S, $S_P$)-10 and (S, $R_P$)-10) and 2

To a 50 mL of dry round-bottomed flask were added 80 mg (0.255 mmol) of 2 and 1 mL of anhydrous tetrahydrofuran. The suspension was cooled in an ice-water bath and a solution of Grignard reagent (1 M in THF, 0.32 mmol) was added via a syringe. The clear solution thus formed was stirred at 0° C. for half hour and then a solution of phosphorus reagent (120 mg, 0.296 mmol, mixture of isomers) in 1 mL of THF was added dropwise at 0° C. The mixture was stirred at room temperature for 44 hours and quenched by addition of 1 N diluted HCl. After aqueous work-up as usual, the crude residue was purified via column chromatography (silica gel, 3% methanol in DCM) to afford 33.9 mg (0.058 mmol, 22.8%) of 1 and its $R_P$-isomer as a 1:1 mixture of two isomers.

Example 12-5

Synthesis of (S)-2-{[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester diastereomeric mixture (1 and its $R_P$-isomer) via diastereomeric mixture of (2S)-isopropyl 2-(((2,4-dichlorophenoxy)(phenoxy)phosphoryl)amino)propanoate ((S, $S_P$)-11 and (S, $R_P$)-11)

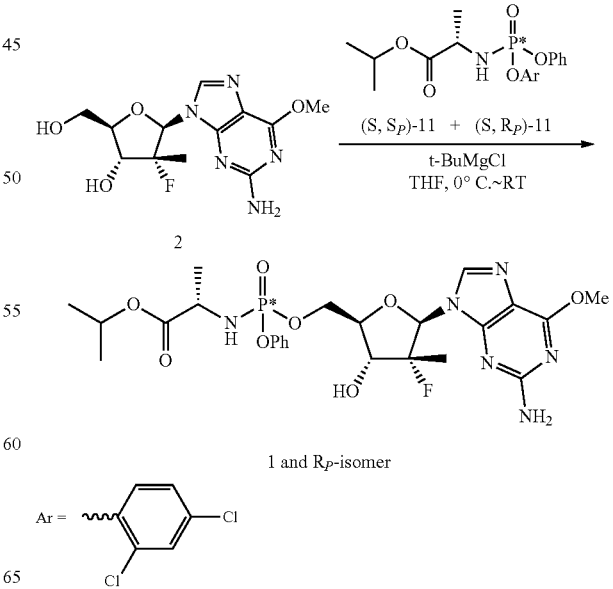

a) Preparation of (2S)-isopropyl 2-(((2,4-dichlorophenoxy)(phenoxy)phosphoryl)amino)propanoate diastereomeric mixture ((S, S$_P$)-11 and (S, R$_P$)-11)

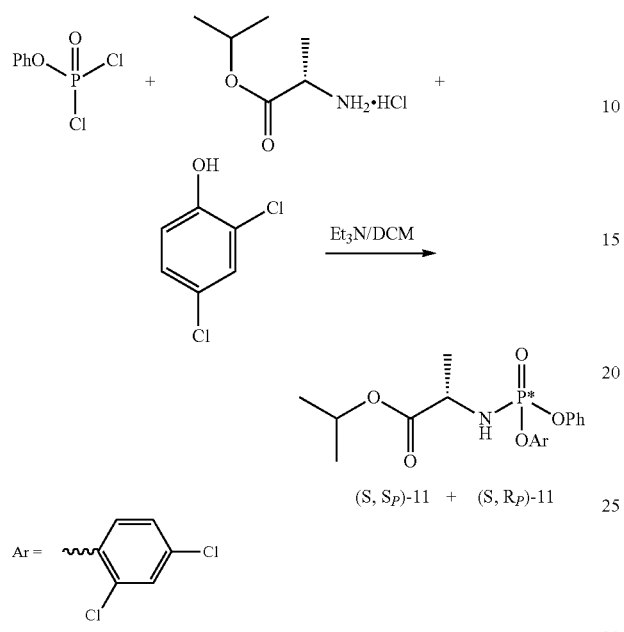

Phenyl phosphorodichloridate (10.0 g, 47.4 mmol) was dissolved in 60 mL of dry DCM and subsequently cooled to −78° C. Slow addition of a preformed mixture of 2,4-dichlorophenol (7.73 g, 47.4 mmol) and triethylamine (7.27 mL, 52.1 mmol) in 20 mL of DCM was followed by stirring at above temperature for 30 min. The reaction was brought to 0° C. and stirred for 2.5 h at this temperature before (L)-alanine isopropyl ester (7.95 g, 47.4 mmol) was added as a solid in one batch. Stirring for 40 min at 0° C. was then followed by addition of more triethylamine (13.9 mL, 99.54 mmol) and additional stirring for 3 h at 0° C. or until judged complete by TLC (ethyl acetate/hexane=1/3). The reaction mixture was subsequently evaporated under reduced pressure and finally submitted to column chromatography (ethyl acetate in hexane) on silica gel to yield the product (mixture of two isomers) in 66% yield (13.6 g) as a viscous colorless oil.

Data: $^1$H NMR (CDCl$_3$, 400 MHz) δ: 7.47-7.44 (m, 1H), 7.42-7.39 (m, 1H), 7.35-7.30 (m, 2H), 7.24-7.15 (m, 3H), 5.05-4.94 (m, 1H), 4.19-4.08 (m, 1H), 3.96-3.89 (m, 1H), 1.41-1.35 (m, 1H), 1.24-1.19 (m, 6H). $^{31}$P NMR (CDCl$_3$, 162 MHz) δ: −1.52 (one isomer), −1.54 (the other isomer).

b) Preparation of Diastereomeric Mixture of 1 and its R$_P$-Isomer from ((S, S$_P$)-11 and (S, R$_P$)-11) and 2

To a dry 50 mL of round-bottomed flask were added 181 mg (0.58 mmol) of 2 and 1.5 mL of anhydrous THF. The suspension was cooled in an ice-water bath. Grignard reagent (1 M solution in THF, 0.72 mmol) was added via a syringe dropwise over 5 minutes at 0° C. The clear solution was stirred at room temperature for half hour before a solution of ((S, S$_P$)-11 and (S, R$_P$)-11) (276 mg, 0.66 mmol) in 1.5 mL of THF was added over 10 minutes. The reaction was allowed to warm up to ambient temperature and stirred for 22 hours. Reaction was not complete and less than half of starting material was consumed. The reaction was quenched after additional three days by adding sat NH$_4$Cl (5 mL). The mixture was diluted with 20 mL of ethyl acetate. After work-up, the residue was purified via column chromatography (silica gel, 4% 2-propanol in DCM) to afford 63.1 mg (0.108 mmol, 19%) of 1 and its R$_P$-isomer as a mixture of two diastereomers. From column, 29.6 mg (0.094 mmol) of starting nucleoside was recovered.

Example 12-6

Synthesis of (S)-2-{[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester diastereomeric mixture (1 and R$_P$-isomer) via (2S)-isopropyl 2-(((2-chloro-4-nitrophenoxy)(phenoxy)phosphoryl)amino)propanoate ((S, S$_P$)-12 and (S, R$_P$)-12)

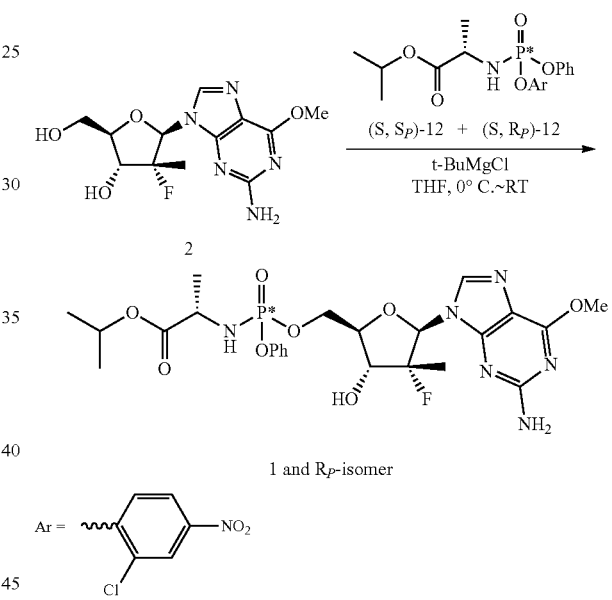

a) Preparation of ((S, S$_P$)-12 and (S, R$_P$)-12) and isolation of (S, S$_P$)-12 and (S, R$_P$)-12

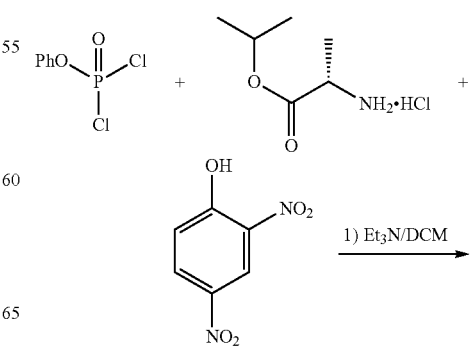

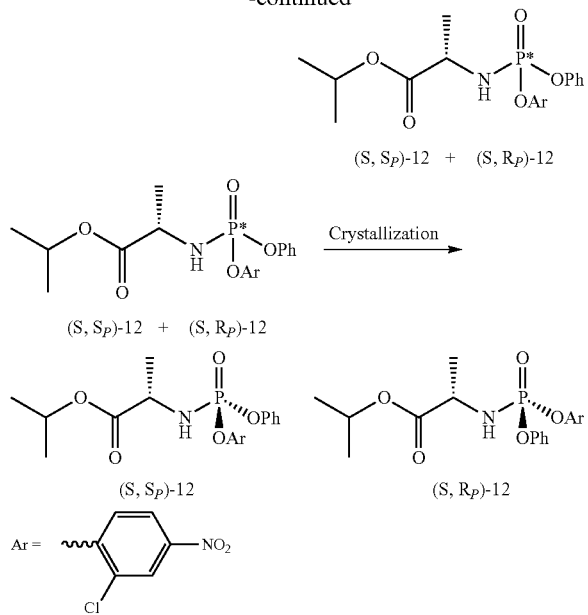

(S, S$_P$)-12 + (S, R$_P$)-12

(S, S$_P$)-12

(S, R$_P$)-12

Ar =  <br>(3-chloro-4-nitrophenyl group)

Phenyl phosphorodichloridate (10.0 g, 47.3 mmol) was dissolved in 50 mL of dry DCM and subsequently cooled to 0° C. After addition of solid (L)-alanine isopropyl ester HCl salt (7.94 g, 47.3 mmol), the reaction mixture was cooled to −70° C. and then treated with triethylamine (13.8 mL, 94.6 mmol) dissolved in 50 mL of dry DCM. The resulting mixture was stirred for 30 min at this temperature before being allowed to warm to 0° C. Subsequently, a preformed solution of 2-chloro-4-nitrophenol (8.2 g, 47.3 mmol) and triethylamine (6.6 mL, 47.3 mmol) dissolved in 20 mL of dry DCM was added over 5-10 min and was continued stirring for additional 2 h. The solution was filtered and the filtrate was concentrated under reduced pressure. The resulting residue was suspended in 50 mL of TBME and stirred for 10 min at room temperature. Subsequent filtration removed more triethylamine hydrochloride and yielded a filtrate that was again stripped of its solvent under reduce pressure. Column chromatography (dichloromethane) yielded the product (12.2 g, 27.6 mmol) as solid. The product was recrystallized using EtOAc/hexane (2:3) for two times to isolate (S, R$_P$)-12 (5.2 g, 25% yield) and upon cooling the mother liquor to −5° C. (S, S$_P$)-12 was obtained (1.5 g, 7% yield).

(S, S$_P$)-12 Data: $^1$H NMR (CDCl$_3$, 400 MHz) δ: 8.33 (m, 1H), 8.13-8.10 (m, 1H), 7.73-7.71 (m, 1H), 7.36-7.33 (m, 2H), 7.25-7.18 (m, 3H), 5.00 (hepta, 1H), 4.19-4.10 (m, 1H), 4.02-3.97 (m, 1H), 1.43 (d, 3H), 1.23-1.21 (m, 6H).

$^{31}$P NMR (CDCl$_3$, 162 MHz) δ: −1.97.

(S, R$_P$)-12 Data: $^1$H NMR (CDCl$_3$, 400 MHz) δ: 8.32-8.31 (m, 1H), 8.13-8.10 (m, 1H), 7.73-7.71 (m, 1H), 7.38-7.34 (m, 2H), 7.28-7.19 (m, 3H), 5.02 (hepta, 1H), 4.21-4.11 (m, 1H), 4.01-3.95 (m, 1H), 1.40 (d, 3H), 1.25-1.22 (m, 6H).

$^{31}$P NMR (CDCl$_3$, 162 MHz) δ: −2.02.

b) Preparation of Diastereomeric Mixture of 1 and its R$_P$-Isomer from ((S, S$_P$)-12 and (S, R$_P$)-12) and 2

To a dry 50 mL of round-bottomed flask were added 181 mg (0.58 mmol) of 2 and 1.5 mL of anhydrous THF. The suspension was cooled in an ice-water bath under nitrogen. Grignard reagent (1 M solution in THF, 0.72 mmol) was added via a syringe and a clear solution was formed. The mixture was stirred at ambient temperature for half hour and then cooled to 0° C. again. A solution of ((S, S$_P$)-12 and (S, R$_P$)-12) (292 mg, 0.66 mmol) in 1.5 mL of THF was added via a syringe over 10 minutes at 0° C. The resulting orange color reaction solution was stirred at room temperature for overnight (19 h) and reaction was almost complete as checked by TLC. The reaction was quenched by addition of sat NH$_4$Cl (5 mL) and diluted with 20 mL of ethyl acetate and 10 mL of water. Two layers were separated and aqueous layer was extracted with 20 mL of EtOAc. Organic layer was washed with water (20 mL), sat sodium bicarbonate (2×30 mL), 5% sodium carbonate (30 mL), water (20 mL), and brine (20 mL). Organic solution was dried over sodium sulfate and concentrated to a yellow color solid residue. The residue was purified via column chromatography (silica gel, 3% methanol in DCM) to afford 279 mg (0.48 mmol, 83%) of 1 and its R$_P$-isomer.

Example 12-7

Synthesis of (S)-2-{(R)-[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester (R$_P$-isomer of 1) via (2S)-isopropyl 2-(((R)-(2-chloro-4-nitrophenoxy)(phenoxy)phosphoryl)amino) propanoate ((S, R$_P$)-12)

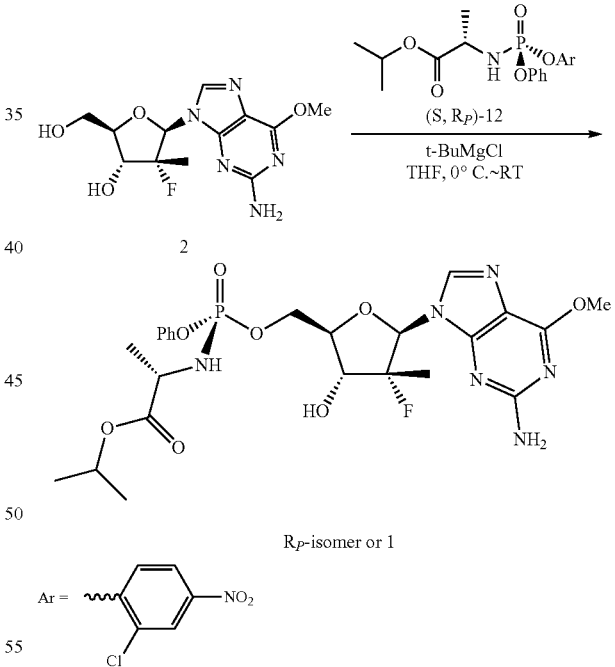

Ar =  <br>(3-chloro-4-nitrophenyl group)

To a 50 mL of dry round-bottomed flask were charged 70 mg (0.223 mmol) of 2 and 1 mL of anhydrous THF. The flask was cooled in an ice-water bath and Grignard reagent (1 M solution in THF, 0.32 mL) was added dropwise at 0° C. After stirred at 0° C. for half hour, a solution of the (S, R$_P$-12) (129 mg, 0.29 mmol) in 1 mL of THF was added via a syringe. A clear brown color solution was formed and gradually warmed up to ambient temperature. After overnight (19 h) at room temperature, the reaction was quenched by adding 1 N of diluted HCl at 0° C. The mixture was diluted with ethyl acetate (20 mL) and water (10 mL). After separation of two layers, aqueous layer was extracted with EtOAc (10 mL). Organic layer was washed with water (10 mL), sat sodium bicarbonate (3×15 mL), water (10 mL), brine (10 mL), and dried over sodium sulfate. After concentration, the solid residue was purified via column chromatography (silica gel, 3% methanol in DCM) to afford 100 mg (0.17 mmol, 77%) of product as a white solid and single isomer.

Example 12-8

Synthesis of (S)-2-{[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester diastereomeric mixture (1+R$_P$-isomer of 1) via diastereomeric mixture (2S)-isopropyl 2-((phenoxy(2-thioxobenzo[d]thiazol-3(2H)-yl)phosphoryl)amino) propanoate ((S, S$_P$)-13 and (S, R$_P$)-13)

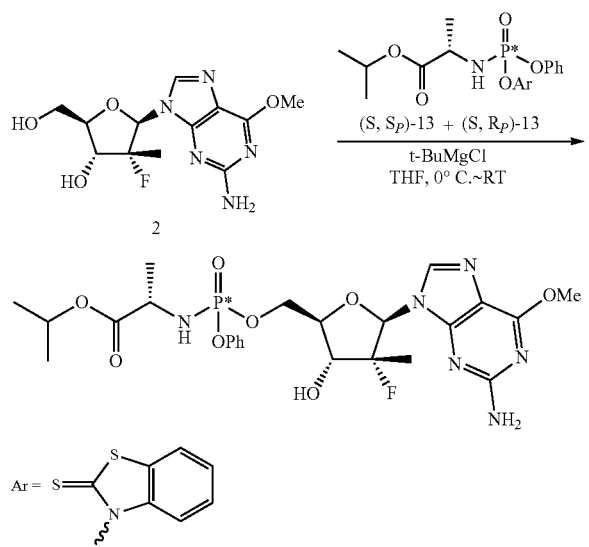

a) Preparation of ((S, S$_P$)-13 and (S, R$_P$)-13)

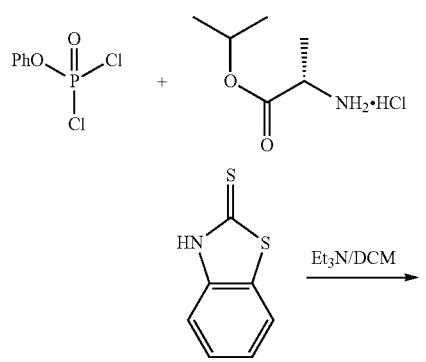

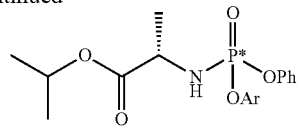

(S, S$_P$)-13 + (S, R$_P$)-13

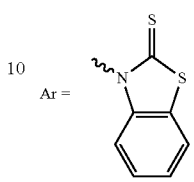

Ar =

Phenyl phosphorodichloridate (6.37 g, 30.19 mmol) was dissolved in 40 mL of dry DCM and subsequently cooled to 0° C. After addition of solid (L)-alanine isopropyl ester (5.06 g, 30.19 mmol), the reaction mixture was cooled to −78° C. and then treated with triethylamine (8.84 mL, 63.3 mmol) dissolved in 20 mL of dry DCM. The resulting mixture was stirred for 30 min at this temperature before being allowed to warm to 0° C. Subsequently, a preformed solution of benzo[d]thiazole-2(3H)-thione (5.05 g, 30.19 mmol) and triethylamine (4.63 mL, 33.21 mmol) dissolved in 20 mL of dry DCM was added over 5-10 min whereupon the mixture was allowed to warm to RT over night. The cloudy mixture was then cooled back to 0° C. and filtered to remove all solids. The filtrate was stripped of all solvent under reduced pressure. The resulting residue was suspended in 50 mL of TBME and stirred for 1 h at RT. Subsequent filtration removed more triethylamine hydrochloride and yielded a filtrate that was again stripped of its solvent under reduce pressure. Column chromatography (DCM) yielded ((S, S$_P$)-13 and (S, R$_P$)-13) (3:1, isomer I/isomer II) in 15% (1.97 g) yield as viscous oil.

Data: $^1$H NMR (CDCl$_3$, 300 MHz) δ: 8.63-8.59 (m, 1H), 7.37-7.27 (m, 7H), 7.18-7.14 (m, 1H), 6.05-5.97 (m, 1H), 5.04 (hepta, 1H, isomer II), 4.91 (hepta, 1H, isomer I), 4.37-4.24 (m, 1H), 1.45-1.42 (d, 3H, isomer I), 1.41-1.39 (d, 3H, isomer II), 1.26-1.22 (m, 6H), 1.09-1.02 (m, 6H). $^{31}$P NMR (CDCl$_3$, 121 MHz) δ: −0.43 (isomer I), −1.29 (isomer II).

b) Preparation of Diastereomeric Mixture of 1 and its R$_P$-isomer from ((S, S$_P$)-13 and (S, R$_P$)-13) and 2

To a dry round-bottomed flask were added 120 mg (0.38 mmol) of 2 and 1.5 mL of anhydrous THF. The mixture was cooled to 0° C. and 0.5 mL of Grignard reagent (0.5 mmol) was added dropwise. The clear solution was stirred at 0° C. for half hour. A solution of ((S, S$_P$)-13 and (S, R$_P$)-13) (197 mg, 0.45 mmol) in 1.5 mL of THF was added via a syringe. The resulting mixture was allowed to warm up to room temperature and stirred for overnight (19 h). TLC showed reaction was not complete and product was found together with bis-phosphoramidate by-product. Reaction was quenched by addition of 1 N of diluted HCl at 0° C. and mixture was diluted with 20 mL of ethyl acetate. After work-up, as noted above, an oily residue was obtained and it was purified via column chromatography (silica gel, 3% methanol in DCM) to afford 78.6 mg (0.13 mmol, 35%) of 1 and its R$_P$-isomer as a mixture of two diastereomers. From column, 36.4 mg of bis-phosphoramidate by-product was isolated.

Example 13

Biological Data of Compound 1

HCV replicon assay. HCV replicon RNA-containing Huh7 cells (clone A cells; Apath, LLC, St. Louis, Mo.) were kept at exponential growth in Dulbecco's modified Eagle's medium (high glucose) containing 10% fetal bovine serum, 4 mM L-glutamine and 1 mM sodium pyruvate, 1× nonessential amino acids, and G418 (1,000 µg/ml). Antiviral assays were performed in the same medium without G418. Cells were seeded in a 96-well plate at 1,500 cells per well, and test compounds were added immediately after seeding. Incubation time 4 days. At the end of the incubation step, total cellular RNA was isolated (RNeasy 96 kit; Qiagen). Replicon RNA and an internal control (TaqMan rRNA control reagents; Applied Biosystems) were amplified in a single-step multiplex RT-PCR protocol as recommended by the manufacturer. The HCV primers and probe were designed with Primer Express software (Applied Biosystems) and covered highly conserved 5'-untranslated region (UTR) sequences (sense, 5'-AGCCATGGCGTTAGTA(T)GAGTGT-3' (SEQ ID NO: 1), and antisense, 5'-TTCCGCA-GACCACTATGG-3' (SEQ ID NO: 2); probe, 5'-FAM-CCTCCAGGACCCCCCCTCCC -TAMRA-3') (SEQ ID NO: 3).

To express the antiviral effectiveness of a compound, the threshold RT-PCR cycle of the test compound was subtracted from the average threshold RT-PCR cycle of the no-drug control ($\Delta Ct_{HCV}$). A $\Delta Ct$ of 3.3 equals a 1-log 10 reduction (equal to the 90% effective concentration [$EC_{90}$]) in replicon RNA levels. The cytotoxicity of the test compound could also be expressed by calculating the $\Delta Ct_{rRNA}$ values. The $\Delta\Delta Ct$ specificity parameter could then be introduced ($\Delta Ct_{HCV}-\Delta Ct_{rRNA}$), in which the levels of HCV RNA are normalized for the rRNA levels and calibrated against the no-drug control. Compound 1 was tested for its biological properties based on the preceding assay. The results of these tests are disclosed below.

| Compd. No. | CloneA $EC_{90}$ (µM) |
|---|---|
| 1 | 0.02 |

Replicon assay results show activity when compound 1 is assayed in combination with compound C (designated as compound 19 in US 2010/0081628, and the individual diastereomers (19a and 19b) disclosed in the same application); compound D (disclosed in US 2010/0016251); compound E (disclosed in U.S. Ser. No. 12/783,680 as Sp-4); ITMN-191 (disclosed in US 2009/0269305 at Example 62-1); and ANA-598 (disclosed in F. Ruebasam et al. Biorg. Med. Chem. Lett. (2008) 18: 3616-3621 as compound 31). Surprisingly, replicon assay results show synergism when compound 1 is assayed in combination with any one of compound C (19a or 19b); compound E ($S_P$-4), ITMN-191; and ANA-598.

This application claims priority to U.S. 61/319,513, filed on Mar. 31, 2010; U.S. 61/319,548, filed on Mar. 31, 2010; and U.S. 61/355,940, filed on Jun. 17, 2010, the subject matter of which is incorporated by reference in its entirety.

The contents of U.S. Provisional Patent Application No. 61/319,548 and U.S. patent application Ser. No. 12/645,765, filed on Dec. 23, 2009; Ser. No. 12/053,015, filed on Mar. 21, 2008; Ser. No. 12/783,680, filed on May 20, 2010; and Ser. No. 13/076,552, filed on Mar. 31, 2011 are hereby incorporated by reference in their entirety. Moreover, the patent and non-patent references disclosed herein are incorporated by reference. In the event that the incorporated subject matter contains a term that conflicts with a term disclosed in the present application text, the meaning of the term contained in the present application controls provided that the overall meaning of the incorporated subject matter is not lost.

The invention claimed is:

1. A compound represented by formula 1, its hydrate or solvate thereof in crystalline or crystal-like form.

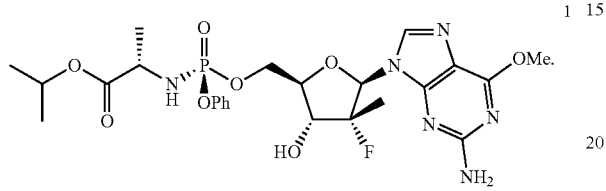

2. The compound of claim 1, represented by 1.mH$_2$O, wherein m varies in an integer or non-integer amount from about 0 to about 5 and is not 0.

3. The compound of claim 2, wherein m is about 1.

4. The compound of claim 2, wherein m is about ½.

5. The compound of claim 2, wherein m is about 1, that further comprises an amount of adsorbed water.

6. The compound of claim 5, wherein the amount of adsorbed water ranges from about 0 wt. % to about 10 wt. % based on the weight of the 1.H$_2$O.

7. The compound of claim 2, wherein the compound is a monohydrate in crystalline form.

8. The compound of claim 7 having an XRPD 2θ-reflection (°) at about 14.8.

9. The compound of claim 8 having XRPD 2θ-reflections (°) at about 14.8 and about 17.6.

10. The compound of claim 9 having XRPD 2θ-reflections (°) at about 20.4.

11. The compound of claim 9 having XRPD 2θ-reflections (°) at about 8.7.

12. The compound of claim 9 having XRPD 2θ-reflections (°) at about 13.6.

13. The compound of claim 9 having XRPD 2θ-reflections (°) at about.

14. The compound of claim 9 having a pattern substantially as that shown in FIG. 1.

15. The compound of claim 7, wherein the compound is an orthorhombic crystalline.

16. The orthorhombic crystalline of claim 15, having the following unit cell parameters a~10.99 Å, b~13.09 Å, and c~20.36 Å.

17. A composition comprising the compound of claim 1.

18. A method for treating HCV in a patient in need thereof, which comprises administering to the patient a therapeutically effective amount of the compound of claim 1.

19. A method for treating HCV in a patient in need thereof, which comprises administering to the patient a therapeutically effective amount of the compound of claim 7.

20. A method for treating HCV in a patient in need thereof, which comprises administering to the patient a therapeutically effective amount of the compound of claim 1 in combination or in alternation with a therapeutically effective amount of another antiviral.

21. The method of claim 20, wherein the other antiviral is selected from the group consisting of

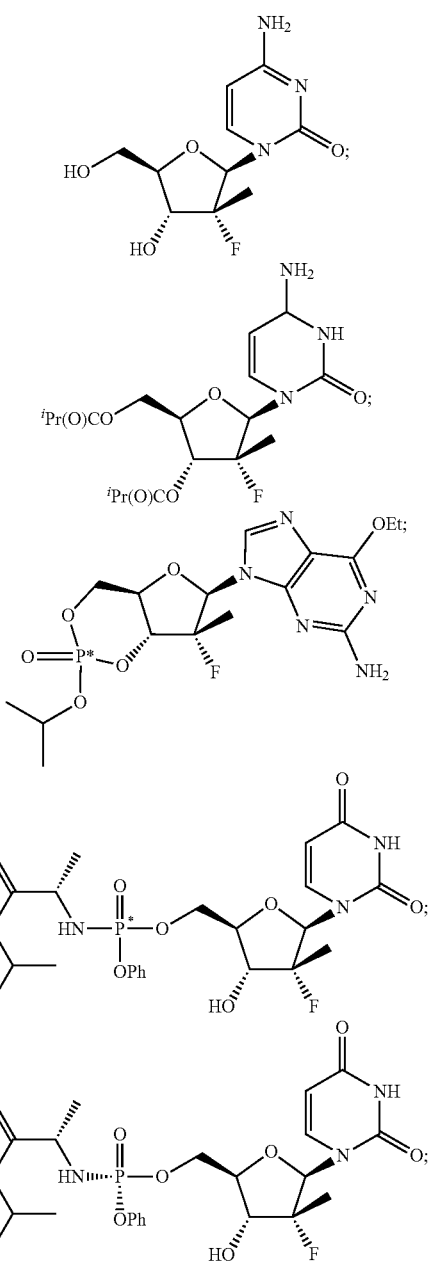

telaprevir; boceprevir; BMS-790052; ITMN-191; ANA-598; TMC435; and combinations thereof.

22. A co-therapy method for treating HCV in a patient in need thereof, which comprises administering to the patient a therapeutically effective amount of the compound of claim 7 in combination or in alternation with a therapeutically effective amount of another antiviral.

23. The co-therapy method of claim 22, wherein the other antiviral is selected from the group consisting of

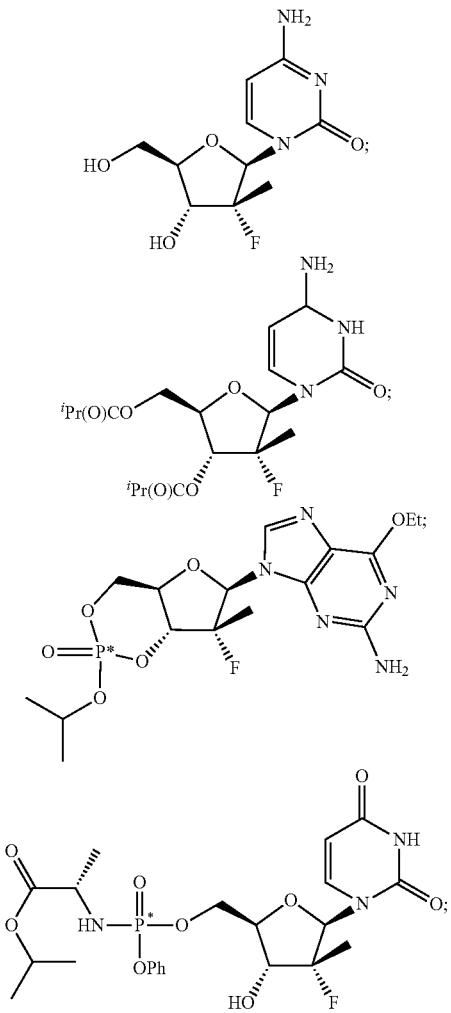
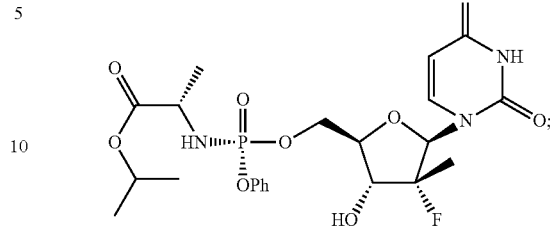

telaprevir; boceprevir; BMS-790052; ITMN-191; ANA-598; TMC435; and combinations thereof.

24. A process for preparing the compound of claim 1 in a crystalline form, which comprises crystallizing the compound of claim 1.

25. The process of claim 24, which further comprises dissolving or suspending the compound of claim 1 in a solvent or solvent mixture.

26. The process of claim 25, wherein the solvent or solvent mixture is selected from the group consisting of anisole, ethyl acetate; xylenes; toluene; isopropanol; acetone; dichloromethane; diethyl ether; isopropyl acetate; t-butyl methyl ether; and combinations thereof.

27. The process of claim 25, wherein the solvent mixture is selected from the group consisting of anisole/ethyl acetate; heptanes/ethyl acetate; xylenes/ethyl acetate/water; anisole/water; ethyl acetate/xylenes; isopropanol/xylenes; acetone/xylenes; dichloromethane/xylenes; dichloromethane/hexanes; ethyl acetate/toluene; diethyl ether/xylenes; isopropyl acetate/xylenes; isopropyl acetate/heptanes; ethyl acetate/water; t-butyl methyl ether/water; and t-butyl methyl ether/ethyl ether.

28. A method for determining the crystallinity of the compound of claim 1, which comprises analyzing the compound by XRPD or single-crystal X-ray crystallography.

* * * * *

UNITED STATES PATENT AND TRADEMARK OFFICE
CERTIFICATE OF CORRECTION

PATENT NO. : 8,563,530 B2  
APPLICATION NO. : 13/076718  
DATED : October 22, 2013  
INVENTOR(S) : Wonsuk Chang et al.

Page 1 of 1

It is certified that error appears in the above-identified patent and that said Letters Patent is hereby corrected as shown below:

Title Page

Item [73] Assignee, Please replace "Gilead Pharmassel LLC" with --Gilead Pharmasset LLC--.

Signed and Sealed this  
Sixth Day of May, 2014

Michelle K. Lee  
*Deputy Director of the United States Patent and Trademark Office*